(12) United States Patent
Buck et al.

(10) Patent No.: US 11,896,759 B2
(45) Date of Patent: *Feb. 13, 2024

(54) INHALERS AND RELATED METHODS

(71) Applicant: Norton (Waterford) Limited, Waterford (IE)

(72) Inventors: Daniel Buck, County Waterford (IE); Paul Prendergast, County Carlow (IE); Declan Walsh, County Kilkenny (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/949,483

(22) Filed: Sep. 21, 2022

(65) Prior Publication Data

US 2023/0012966 A1    Jan. 19, 2023

Related U.S. Application Data

(63) Continuation of application No. 15/881,358, filed on Jan. 26, 2018, now Pat. No. 11,559,637.

(30) Foreign Application Priority Data

Feb. 14, 2017    (GB) ...................................... 1702408

(51) Int. Cl.
*A61M 15/00* (2006.01)
*A61M 15/08* (2006.01)
(Continued)

(52) U.S. Cl.
CPC ......... *A61M 15/0025* (2014.02); *A61K 9/007* (2013.01); *A61K 31/439* (2013.01);
(Continued)

(58) Field of Classification Search
CPC .... A61K 9/007; A61K 31/439; A61K 31/569; A61M 15/0021; A61M 15/0025;
(Continued)

(56) References Cited

U.S. PATENT DOCUMENTS 4,091,948 A    5/1978 Northup
4,375,858 A    3/1983 Shah et al.
(Continued)

FOREIGN PATENT DOCUMENTS

EP    1289589 A    3/2003
EP    2135199 A    5/2012
(Continued)

OTHER PUBLICATIONS

Label for QVAR® Redihaler™ revised in 2017; 26 pages.
(Continued)

*Primary Examiner* — Colin W Stuart
*Assistant Examiner* — Matthew D Ziegler
(74) *Attorney, Agent, or Firm* — Morgan, Lewis & Bockius LLP

(57) ABSTRACT

An inhaler (10) has a main body for accommodating a medicament reservoir (84), a canister fire system for moving a canister (50) to release a dose in response to air flow, a cap housing (12) for enclosing the canister fire system and canister within an interior chamber defined by the main body (14) and a cap housing, wherein a lock system (250) is provided for locking the cap housing on the main body.

44 Claims, 21 Drawing Sheets

(51) Int. Cl.
| | |
|---|---|
| *A61P 11/00* | (2006.01) |
| *A61P 11/06* | (2006.01) |
| *A61K 31/569* | (2006.01) |
| *A61K 31/439* | (2006.01) |
| *A61K 9/00* | (2006.01) |
| *B65D 41/04* | (2006.01) |
| *B65D 55/16* | (2006.01) |

(52) U.S. Cl.
CPC ......... *A61K 31/569* (2013.01); *A61M 15/009* (2013.01); *A61M 15/0021* (2014.02); *A61M 15/0066* (2014.02); *A61M 15/0071* (2014.02); *A61M 15/0091* (2013.01); *A61M 15/08* (2013.01); *A61P 11/00* (2018.01); *A61P 11/06* (2018.01); *B65D 41/0414* (2013.01); *B65D 41/0428* (2013.01); *B65D 55/16* (2013.01); *A61M 15/0026* (2014.02); *A61M 15/0076* (2014.02); *A61M 2205/18* (2013.01)

(58) Field of Classification Search
CPC .......... A61M 15/0026; A61M 15/0066; A61M 15/0071; A61M 15/0076; A61M 15/009; A61M 15/0091; A61M 15/08; A61M 2205/18; A61P 11/00; A61P 11/06; B65D 41/0414; B65D 41/0428; B65D 55/16
See application file for complete search history.

(56) References Cited

U.S. PATENT DOCUMENTS

| | | | |
|---|---|---|---|
| 4,413,755 A | 11/1983 | Brunet | |
| 5,060,643 A * | 10/1991 | Rich | A61M 15/0091 128/200.14 |
| 5,611,444 A | 3/1997 | Garby et al. | |
| 5,776,432 A | 7/1998 | Schultz et al. | |
| 6,170,717 B1 | 1/2001 | Di Giovanni et al. | |
| 6,318,603 B1 | 11/2001 | Burt | |
| 6,345,740 B1 | 2/2002 | Riebe | |
| 6,446,626 B1 | 9/2002 | Virtanen | |
| 6,446,627 B1 | 9/2002 | Bowman et al. | |
| 6,454,140 B1 | 9/2002 | Jinks | |
| 6,644,517 B2 | 11/2003 | Thiel et al. | |
| 6,848,590 B2 | 2/2005 | Brozell et al. | |
| 7,278,556 B2 | 10/2007 | Goujon et al. | |
| 7,637,260 B2 | 12/2009 | Holroyd | |
| 7,793,805 B2 | 9/2010 | Allsop | |
| 7,814,900 B2 * | 10/2010 | Bacon | A61M 15/0091 128/200.14 |
| 7,819,264 B2 | 10/2010 | Brozell et al. | |
| 7,886,934 B2 | 2/2011 | Lu et al. | |
| 7,959,042 B2 | 6/2011 | Twyman | |
| 8,132,712 B2 | 3/2012 | Fenlon | |
| 8,235,044 B2 | 8/2012 | Fletcher | |
| 8,286,941 B2 | 10/2012 | Fontela et al. | |
| 8,434,648 B2 | 5/2013 | Marie et al. | |
| 8,931,476 B2 | 1/2015 | Kaar et al. | |
| 8,973,784 B2 | 3/2015 | Lu et al. | |
| 9,067,031 B2 | 6/2015 | Jinks et al. | |
| 9,096,371 B2 | 8/2015 | Allsop | |
| 9,346,590 B2 | 5/2016 | Ramsey | |
| 9,572,945 B2 | 2/2017 | Duignan et al. | |
| 2002/0043262 A1 | 4/2002 | Langford et al. | |
| 2002/0153005 A1 | 10/2002 | Scarrott et al. | |
| 2003/0042336 A1 | 3/2003 | Wuttke et al. | |
| 2005/0209558 A1 | 9/2005 | Marx | |
| 2005/0242055 A1 | 11/2005 | Oh | |
| 2005/0284474 A1 | 12/2005 | Tseng | |
| 2006/0243275 A1 | 11/2006 | Ruckdeschel et al. | |
| 2007/0119450 A1 | 5/2007 | Wharton et al. | |
| 2008/0230505 A1 | 9/2008 | Kerman et al. | |
| 2013/0298907 A1 | 11/2013 | Zuyderhoudt | |
| 2014/0096769 A1 | 4/2014 | Walsh et al. | |
| 2014/0373832 A1 | 12/2014 | Zeng et al. | |
| 2015/0157815 A1 | 6/2015 | Bacon | |
| 2016/0084385 A1 | 3/2016 | Petit et al. | |
| 2016/0151588 A1 | 6/2016 | Miller et al. | |
| 2016/0243319 A1 | 8/2016 | Szymiczek et al. | |
| 2016/0376088 A1 | 12/2016 | Jacuk | |
| 2017/0095626 A1 | 4/2017 | Pieters | |
| 2017/0173280 A1 | 6/2017 | Howgill | |

FOREIGN PATENT DOCUMENTS

| | | |
|---|---|---|
| EP | 2514464 A | 10/2012 |
| EP | 2514465 A | 10/2012 |
| WO | 1993024167 A1 | 12/1993 |
| WO | 2007022573 A1 | 3/2007 |
| WO | 2008030837 A1 | 3/2008 |
| WO | 2012072249 A1 | 6/2012 |
| WO | 2013064820 A2 | 5/2013 |
| WO | 2016090152 A1 | 6/2016 |

OTHER PUBLICATIONS

Communication pursuant to Article 94(3) EPC dated May 11, 2021 for European Patent Application No. 18702228.0, 6 pages.
Extended Search Report dated Sep. 1, 2022, for European Patent Application No. 22159182.9, 11 pages.

* cited by examiner

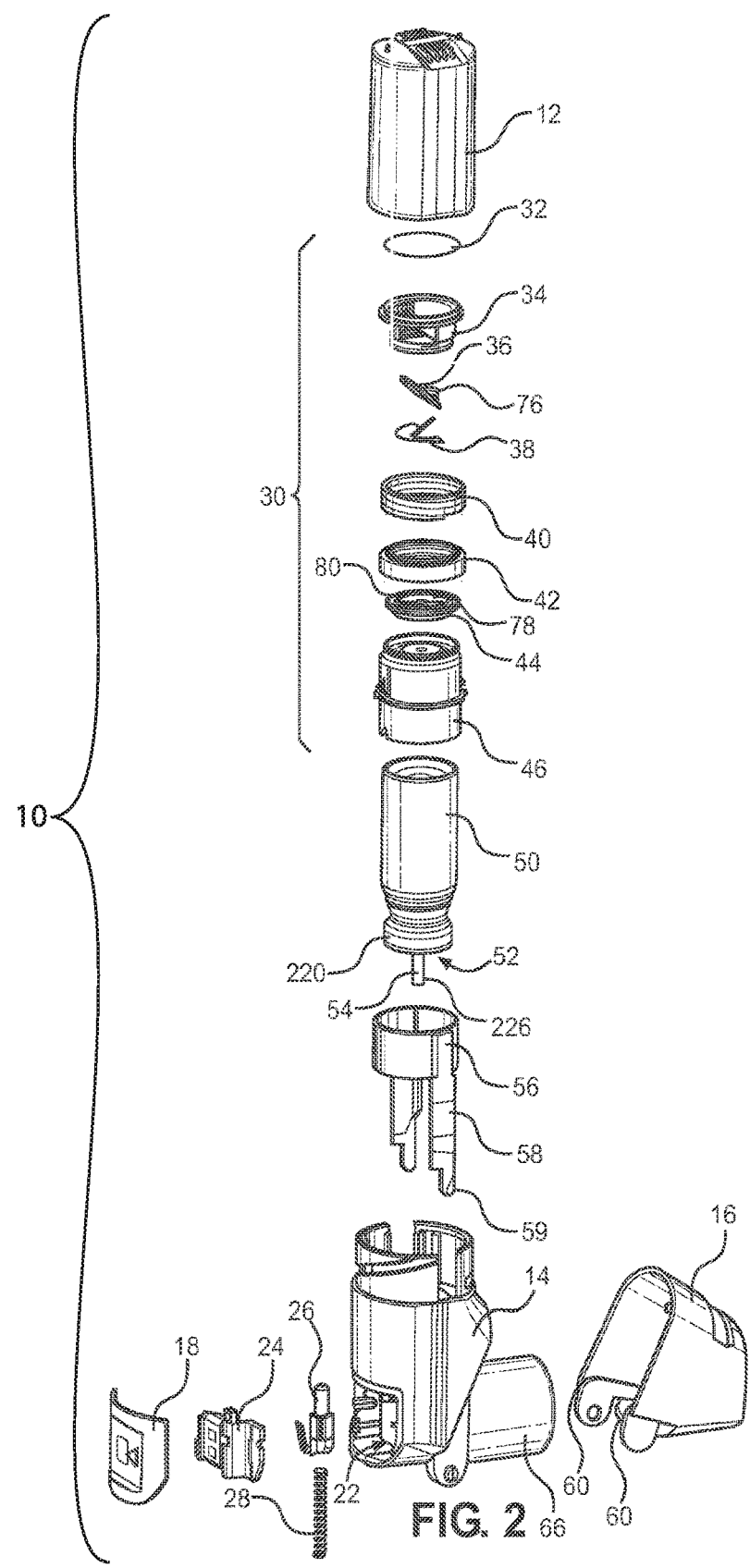

INHALERS AND RELATED METHODS

CROSS-REFERENCE TO RELATED APPLICATIONS

This application is a continuation application of U.S. Nonprovisional patent application Ser. No. 15/881,358, filed Jan. 26, 2018, which claims the benefit of Application No. GB1702408.4, filed Feb. 14, 2017, each of which is incorporated by reference herein in its entirety and for all purposes.

FIELD OF THE INVENTION

The present invention relates to inhalers, including breath actuated and metered dose inhalers. The invention relates to oral and nasal inhalers. The invention also relates to methods of metering inhalable substances in metering valves of canisters for medicament inhalers, inhaler housings and inhaler valve stem and valve stem block interfaces.

BACKGROUND OF THE INVENTION

A known inhaler, which is a breath actuated inhaler, has a pressurised canister and a metering valve for controlling the ejection of inhalable substances from the canister. The canister is operable by a force holding unit having a cap housing attachable to a main housing of the inhaler. The metering valve includes a valve stem for transferring substances from an interior reservoir of the canister into the metering chamber and then out of the metering chamber along the valve stem in the direction of a nozzle of the inhaler. A radially directed capillary port is provided in the valve stem for communicating substances out of the interior reservoir for communication along the valve stem to the metering chamber and a similar port is provided for communicating substances out of the metering chamber and along the valve stem towards the nozzle. In use, a mouthpiece cap is opened to ready the inhaler for inhalation and then after inhalation the mouthpiece cap is closed and resets a canister fire system. It has been found that the inhaler can be left after inhalation with the mouthpiece dust cap in the opened position with the metering chamber communicating with atmosphere via the valve stem and nozzle. This can result in the variance of active ingredients in at least one subsequent dose. This means that users will sometimes remove a force holding unit cap housing from the main body of the inhaler and try to ensure that the metering chamber is sufficiently primed by firing a number of doses and this is both wasteful and may result in damage to the inhaler.

In some inhalers, when it is necessary to make changes to internal components, it is difficult to provide space and good guidance for all the necessary interior moving parts. Also, the assembly of some inhaler dose counters can be difficult.

Furthermore, in some inhalers, despite a tight connection between the valve stem and a valve stem block within the main body, blowback can occur which is leakage of substances between the valve stem block and valve stem. It can also be difficult in some inhalers to achieve reliable dose counting to reflect the number of doses actually provided by the inhaler.

The present invention aims to alleviate at least to a certain extent at least one of the problems of the prior art.

Alternatively, the present invention aims to provide a useful inhaler, method of metering substances in a metering valve of a canister for a medicament inhaler and/or useful inhaler parts.

SUMMARY OF THE INVENTION

One aspect of the present disclosure discloses a breath actuated inhaler having a main body for accommodating a medicament reservoir, a canister fire system for moving the canister to release a dose in response to air flow, a cap housing for enclosing the canister fire system and canister within an interior chamber defined by the main body and the cap housing, wherein a lock system is provided for locking the cap housing on the main body.

Advantageously, a user can be prevented from tampering with and damaging the interior components of the inhaler. In the case of a breath actuated inhaler, this is particularly advantageous because prior inhalers have required the ability to remove the cap housing for manual priming of the metering chamber. But, when a metering valve is provided with an opening configured to permit flow in a direction with an axial component along the valve stem directly between the transfer space inside the valve stem and the interior reservoir, and when the interior reservoir is arranged for orientation above the metering chamber whereby gas such as air located within the metering chamber is replaced with liquid from the interior reservoir, it is no longer necessary to be able to open the inhaler for manual priming of the metering chamber by manually pushing and firing the canister.

Helical threads may be provided for rotational attachment of the cap housing on the main body and for resisting relative longitudinal movement therebetween without rotation.

The lock system may include a protrusion in the region of a helical thread on one of the main body and the cap housing which is lockable in a recess in the region of a helical thread on the other of the main body and the cap housing.

Two said protrusions may be engageable in two said recesses formed at opposing locations on the inhaler.

Each protrusion may have a leading ramp surface and a trailing ramp surface, the included angle between the ramp and trailing surfaces being about 95° to 120°; the included angle of the protrusion preferably being larger than that of the recess.

The main body may have a central axis and the ramp surfaces are inclined at an angle of about 45° plus or minus 15° (or plus or minus 10°) to tangential.

The lock system may include a first lock member on one of the main body and the cap housing which is adapted to engage a second lock member at a lock interface formed by respective engagement faces thereof, the lock interface being oriented substantially perpendicular to tangential.

The main body may have a central axis and the first lock member has a radial extent of 0.25 to 0.75 mm, preferably about 0.35 to 0.45 mm; the first lock member preferably having a longitudinal extent of about 10 mm.

The main body and the cap housing may be formed of plastics material and the lock system may be configured so that a release torque required to overcome the locking provided by the plastics main body and cap housing is more than 1 Nm.

The lock system may be configured such that the release torque is between 2 and 5 Nm, preferably between 2.5 and 3 Nm, about 2.7 Nm being one example.

According to another, the present disclosure discloses a method of metering inhalable substances in a metering valve of a canister for a medicament inhaler, the method comprising: providing the metering valve with a metering chamber and valve stem extending from a metering chamber to an interior reservoir of the canister, with the valve stem defining a communication path between the metering chamber and the interior reservoir, the communication path including an opening configured to permit flow between a transfer space inside the valve stem and the interior reservoir; and orienting the interior reservoir above the metering chamber and replacing gas such as air located within the metering chamber with liquid from the interior reservoir.

The present inventors have worked out that the reasons why inaccurate dosing can occur include that when the metering chamber is left vented to atmosphere in some prior inhalers for as little as 2 minutes, a gas or air lock can form in the metering chamber and when the metering chamber is next connected for communication with the interior reservoir, due to the radial capillary port, the gas or air is trapped within the metering chamber and liquid does not enter the metering chamber reliably as the next dose. The air may enter the metering chamber from the atmosphere in the prior art. This may happen as propellant in the metering chamber evaporates and diffuses into the atmosphere. Using the presently disclosed method which involves the use of the opening configured to permit flow in a direction with an axial component along the valve stem directly between a transfer space inside the valve stem and the interior reservoir, when the interior reservoir is oriented above the metering chamber, this enables liquid from the interior reservoir to replace gas such as air located within the metering chamber and an accurate dose can be administered at the next dose.

The opening may be configured to permit flow in a direction with an axial component along the valve stem directly between the transfer space inside the valve stem and the interior reservoir.

The replacing gas located in the metering chamber with liquid from the interior reservoir may include flowing liquid under pressure through the opening, along the valve stem to a portion of the communication path communicating with the metering chamber.

The method may include flowing gas from the metering chamber, in a direction counter to a direction of liquid flow from the interior reservoir, along the communication path into the interior chamber.

The method may include providing the opening as an elongated opening.

The method may include providing a second opening to the communication path diametrically opposed to the first said opening.

The method may include providing the valve stem with at least one said opening into the interior reservoir as having an axially oriented opening portion which is oriented facing directly axially along a longitudinal axis of the valve stem into the interior reservoir, and which includes flowing liquid into the metering chamber via said axially oriented opening portion.

The method may include venting the metering chamber to atmosphere via a valve stem block and/or nozzle.

The method may include operating the metering valve and canister within a medicament inhaler and holding the valve stem depressed relative to the canister with the metering chamber vented to atmosphere so as at least partially to permit substances within the metering chamber to vaporise and to permit atmospheric air to enter the metering chamber.

Advantageously, the inhaler can be left for a long period such as 24 hours with the metering chamber communicating with atmosphere and then when the metering chamber is reconnected to the interior reservoir and the interior reservoir is oriented above the metering chamber the metering chamber can fully fill with liquid for the next dose. Advantageously, in a breath actuated inhaler, the features of the method mean therefore that any force holding unit and/or cap housing for the inhaler can be permanently secured or locked on to the inhaler so that users cannot tamper with the interior and there is no need to perform manual priming of the metering valve, which is a necessity in prior art inhalers, before the next dose is taken.

The method may include providing the medicament inhaler as a breath actuated inhaler, and may include, in response to air flow, firing the canister by closing communication between the metering chamber and interior reservoir and opening communication between the metering chamber and atmosphere, the valve stem being held depressed after firing.

The method may include resetting the inhaler to a reset configuration with a reset actuator so as to close communication between the metering chamber and atmosphere and open communication between the metering chamber and the interior reservoir, and carrying out the orienting of the interior reservoir above the metering chamber while the inhaler is in the reset configuration.

The method may include providing the reset actuator as a lever, press button, hinged or rotatable piece, dust cap, nasal outlet cap or mouthpiece cap for the inhaler. Closing the actuator may reset the inhaler. In the case of an oral inhaler the reset actuator may be a dust cap mouthpiece cap. In the case of a nasal inhaler, the reset actuator may take a variety of forms, including but not limited to a dust cap or a movable lever, cap or button. In this case, the carrying out of the orienting of the interior reservoir above the metering chamber being carried out once the reset actuator has been opened to a configuration suitable for inhalation or otherwise operated. Therefore, it can be ensured that right before inhalation, the metering chamber is full of liquid and any gas which may have been in the metering chamber has been drawn into the interior reservoir due to the free flowing communication pathway between metering chamber and interior reservoir.

In an alternative embodiment, the inhaler may include a dust cap or mouthpiece cap which closes communication between the metering chamber and atmosphere but does not reset the inhaler. In these cases, optionally, a separate reset actuator may be provided.

The method may include providing the medicament inhaler as a metered dose inhaler and may include applying a force to the canister to hold the valve stem depressed; and may include subsequently releasing the canister to extend the valve stem and carrying out the orienting of the interior reservoir above the metering chamber.

The method may include providing the inhalable substances as including at least one propellant.

The method may include providing at least one said propellant as a hydrofluoroalkane, such as 1,1,1,2-tetrafluoroethane.

The method may include providing at least one said propellant with a surface tension at 25° C. of about 6 to 10 mN/m, typically about 7 to 9 mN/m, about 8 mN/m being one example.

Advantageously, it has been found that fluid with this surface tension is capable of avoiding gas or air lock in the metering chamber by flowing into the metering chamber when the features of the presently disclosed method are used.

The method may include providing the inhalable substances as including an active ingredient in suspension or in solution, such as beclomethasone dipropionate or tiotropium bromide.

According to a further aspect, the present disclosure discloses a breath actuated inhaler for the inhalation of inhalable substances, the inhaler comprising: a canister having an interior reservoir containing pressurised inhalable substances including fluid; a metering valve including a metering chamber and a valve stem defining a communication path between the metering chamber and the interior reservoir, the communication path including an opening configured to permit flow between a transfer space inside the valve stem and the interior reservoir, the interior reservoir being arranged for orientation above the metering chamber whereby gas such as air located within the metering chamber is replaced with liquid from the interior reservoir.

Advantageously, with this configuration of metering valve there is no need to manually prime the metering chamber by repeatedly firing the canister manually and an accurate next dose can be provided to the metering chamber since a gas or air lock can be avoided. This also means, advantageously, that in a breath actuated inhaler having a force holding unit or cap housing secured to a main body of the inhaler, these components may be locked together so that it is relatively difficult for a user to remove the force holding unit or cap housing and tamper with the interior components. Instead, there is no need to perform manual priming and the inhaler main housing and the cap housing can be permanently locked together enclosing the internal moving parts of the inhaler where they cannot easily be damaged.

The opening may be configured to permit flow in a direction with an axial component along the valve stem directly between a transfer space inside the valve stem and the interior reservoir.

The communication path may be configured to permit liquid to flow under pressure along the communication path to the metering chamber and gas to flow in a reverse direction therealong from the metering chamber into the interior reservoir.

The opening may comprise an elongated opening.

The inhaler may include a second opening or further openings into the communication path.

The second opening may be diametrically opposed to the first said opening.

The valve stem may have at least one opening into the interior reservoir with an axially oriented portion facing directly axially along a longitudinal axis of the valve stem into the interior reservoir for the flow of fluid directly into the communication path in an axial direction along the valve stem.

The inhaler may include a metering chamber exit port for venting the metering chamber to atmosphere via a stem block and/or nozzle.

The inhaler may include a canister fire system for ejecting inhalable substances from the inhaler in response to air flow by closing communication between the metering chamber and the interior reservoir and opening communication between the metering chamber and atmosphere. The canister fire system preferably includes a drive such as a spring for driving the canister relative to the valve stem. The inhaler may have an actuator system for operating the drive, the actuator system optionally including a vacuum chamber having a vacuum release system operable to permit the drive to drive movement of the canister relative to the valve stem. The vacuum release system may be air flow actuatable.

The actuator and/or drive may include or operate as a latch, trigger or switch and may take other forms in other embodiments such as being electromechanical.

The canister fire system may be adapted to depress the valve stem into the canister to cause inhalable substances to be ejected from the inhaler and to hold the valve stem depressed with the metering chamber communicating with atmosphere.

The canister fire system may include a reset actuator which is operable so as to extend the valve stem relative to the canister in order to close communication between atmosphere and the metering chamber and to open communication between the metering chamber and the interior reservoir.

In the case of a nasal inhaler, the reset actuator may, for example, comprise a dust cap or a lever, cap or button. In the case of an oral inhaler, the reset actuator may comprise a dust cap or mouthpiece cap for a mouthpiece of the inhaler. The mouthpiece cap may be closable to permit extension of the valve stem relative to the canister, the mouthpiece cap optionally being hingedly connected to a main housing of the inhaler for camming engagement with at least one drive rod. The drive rod may be associated with a yoke for pushing on a drive element to compress a spring of the drive.

In an alternative embodiment, the inhaler may include a dust cap or mouthpiece cap which closes communication between the metering chamber and atmosphere but does not reset the inhaler. In these cases, optionally, a separate reset actuator may be provided.

The inhaler may include a preventer adapted, after an inhalation has taken place, to prevent a further inhalation until the reset actuator has been operated to extend the valve stem. In the case of a mouthpiece or other cap, this may comprise closing the cap.

Advantageously, the preventer may therefore ensure that the user closes the cap at some time before each inhalation and this in turn means that reliable dosing can be achieved.

The preventer may comprise a warning signaller, such as an audible or visual alarm, dose counter or warning notice, quick reference guide or instructions.

The inhaler may include inhalable substances in the interior reservoir which include at least one propellant.

At least one said propellant may comprise a hydrofluoroalkane, such as 1,1,1,2-tetrafluoroethane.

At least one said propellant may have a surface tension at 25° C. of about 6 to 10 mN/m, typically about 7 to 9 mN/m, about 8 mN/m being one example.

The inhaler may include at least one inhalable substance in the interior reservoir as an active ingredient, for example in suspension or in solution, such as beclomethasone dipropionate or tiotropium bromide.

The inhaler may include a dose counter for counting doses, preferably for making one count with each inhalation of a dose.

The dose counter may include: (a) a tape bearing dose indicia for displaying counts and/or (b) an actuator pin for contact with the canister, or a body movable therewith, for counting doses, and preferably a dose counter chamber separated by a barrier from an inner space of the inhaler for containing the canister, the actuator pin optionally extending out of the dose counter chamber through an aperture in the wall for contact during counting with the canister (or the body movable therewith).

The inhaler may be a breath actuated inhaler.

The inhaler may be a metered dose inhaler.

The inhaler may be an oral inhaler.

The inhaler may be a nasal inhaler.

The inhaler may include a reset actuator which when actuated prevents exposure of the metering chamber to atmosphere, wherein the inhaler provides 75 to 125% of labelled claim for a dose following exposure of the metering chamber to atmosphere for a time period which is more than one minute.

In this case, the reset actuator may be a mouthpiece cap that, when closed, prevents exposure of the metering chamber to atmosphere.

The inhaler may provide 75 to 125% of labelled claim for a dose following exposure of the metering chamber to atmosphere for a time period which is more than two minutes.

The inhaler may provide 75 to 125% of labelled claim for a dose following exposure of the metering chamber to atmosphere for a time period which is one hour, more than one hour, 24 hours or more than 24 hours.

Operation of the inhaler may include, subsequent to closing the mouthpiece, opening the mouthpiece.

The inhaler may include a metering valve spring and an opposing canister spring for drivingly firing the canister, the metering valve spring, canister spring and metering valve being arranged in the inhaler such that an equilibrium of various forces is achieved in at least one ready-to-fire configuration of the inhaler.

In that case, the operation of the inhaler may include at least one suction force, e.g. provided by a pneumatic chamber; the suction force preferably operating against the canister spring.

In another aspect, the present application discloses use of a metering valve for preventing gas lock within a metering chamber of an inhaler having a pressurised canister, the metering valve having a metering chamber and a valve stem extending from the metering chamber to an interior reservoir of the canister, with the valve stem defining a communication path between the metering chamber and the interior reservoir, the communication path including an opening configured to permit flow between a transfer space inside the valve stem and the interior reservoir, in use the interior reservoir being oriented above the metering chamber so as to cause movement through the opening and gas such as air located within the metering chamber to be replaced with liquid from the interior reservoir.

The use may be performed in a breath actuated inhaler. The inhaler may be oral. Nasal inhalers of this type are also envisaged.

The use may be performed in a metered dose inhaler. The metered dose inhaler may be oral or nasal.

According to a further aspect, the present disclosure discloses an inhaler housing for an inhaler for inhalable substances, the inhaler housing being arranged to contain a pressurised canister for sliding motion within a tubular body portion thereof, the inhaler housing having a valve stem block for connection to a valve stem of a pressurised canister, the valve stem block having a top surface, the tubular body portion having at least two mutually opposed guide ribs for guiding canister position within the tubular body portion, the guide ribs having substantially straight guide edges extending substantially parallel to and spaced from one another, each straight guide edge having an upper corner where the straight guide edge meets a further surface of the rib leading outwardly towards an upper rib section near an inner wall of the tubular body portion, at least one of the ribs having its straight guide edge's upper corner positioned a distance D2 in a direction parallel to an axis of the valve stem block along away from the top surface of the valve stem block, a distance between the straight guide edges of the ribs perpendicular to the axis being ID2, and in which the ratio D2/ID2 is less than 0.8.

It has been surprisingly found that ratios below this value enable very efficient and smooth guidance of the canister relative to the inhaler housing in some configurations.

The ratio D2/ID2 may be less than 0.75, about 0.7 being one example.

The further surface of at least one guide rib may extend away from the valve stem block and terminate at a distance D3 from the top surface of the valve stem block in the direction parallel to the axis, the ratio D3/I D2 being less than 0.9 or less than 0.85, about 0.8 being one example.

Each guide rib meets the upper rib section near the inner wall of the tubular body portion at outer rib positions wherein the outer rib positions are a distance ID1 apart in a direction perpendicular to the axis, and in which the ratio ID2/ID1 is between 0.7 and 0.9, typically between 0.75 and 0.85, about 0.78 or 0.8 being two examples.

According to a further aspect, the present disclosure discloses an inhaler housing for an inhaler for inhaling inhalable substances, the inhaler having: a body and a dose counter with an actuation member adapted to drive a dose indication portion of the dose counter against a return spring, the body including a recess for location of an end of the return spring; the recess having a substantially flat reaction surface, a shoulder surface adjacent the reaction surface and an entrance mouth into the reaction surface; wherein a distinct guide surface is provided for guiding the end of the return spring into the recess, the distinct guide surface being wider than the entrance mouth in a direction across the mouth.

This feature of the distinct guide surface being wider than the entrance mouth advantageously assists in assembly of the dose counter into the inhaler since when the return spring is being fitted as part of the dose counter installation it can slide along the distinct guide surface relatively easy into the recess.

The entrance mouth may have at least one chamfered entrance lip, the distinct guide surface having a slanted edge which is an extension of the lip.

The distinct guide surface may be substantially planar. The distinct guide surface may have an edge which intersects with an adjacent curved surface of the body.

At least a portion of the distinct guide surface may comprise a portion of the body which is recessed relative to an adjacent portion of the body.

A further aspect of the present disclosure discloses an inhaler housing for an inhaler for inhaling inhalable substances, the inhaler housing having a tubular portion defining a tubular interior space for containing a pressurised canister containing inhaler substances, a valve stem block for engagement with a valve stem of such a pressurised canister, and a dose counter chamber for containing a dose counter assembly, the dose counter chamber being separated from the tubular interior space by a barrier, the barrier including a stepped upper wall area including at least three steps at different levels.

This configuration advantageously permits enough room for the dose counter in the dose counter chamber and enough room for the movable parts inside the inhaler housing including the pressurised canister and in at least one arrangement has been found to be particularly effective in space saving.

The inhaler may include four said steps.

The steps may be arcuate.

The arcuate steps may have substantially flat areas aligned substantially perpendicular to an axis of the valve stem block as well as part-cylindrical riser surfaces between the substantially flat areas.

The steps may be substantially concentric with an axis of the valve stem block.

The steps may extend around the valve stem block a distance of about 180 degrees.

The material forming the barrier may be of substantially constant thickness substantially throughout the steps.

The dose counter chamber may be formed with at least one heat staking pin for mounting of a dose counter system, the heat staking pin being directly attached to at least two of the steps.

The heat staking pin may be attached to at least one step surface that is oriented substantially perpendicular to an axis of the valve stem block and to at least one and preferably two step risers.

An aperture for a drive pin for actuating the dose counter may be formed through a second furthest step away from the valve stem block.

According to a further aspect, the present disclosure discloses an inhaler valve stem and valve stem block interface for a breath actuated inhaler having a dose counter, a pressurised canister containing inhaler substances including a medicament, which may be in solution or suspension, the valve stem block having a cylindrical inner bore with an inner diameter which is a first diameter, the cylindrical inner bore being for accepting a valve stem with an outer diameter, the valve stem block having a seal in the inner bore with a second diameter which is smaller than the first diameter.

It has been found with this configuration that, surprisingly, better sealing is achieved than with a simple interference fit between a cylindrical outer wall of a valve stem and a cylindrical inner wall of a valve stem block with a larger interference fit. This new configuration has been found to be particularly effective at sealing and avoiding blowback leakage. Especially with regard to the dose counter, the seal permits a relatively low insertion force to be needed to insert the valve stem into the valve stem block and enables very accurate positioning of the valve stem relative to the valve stem block in an axial direction of the valve stem, while at the same time providing a surprisingly effective seal bearing in mind the low insertion force.

The first diameter may be about 3.22 mm.

The first diameter may be about 3.5% larger than the second diameter.

An outer diameter of the valve stem may be smaller than the first diameter but larger than the second diameter prior to introduction of the valve stem into the inner bore, preferably about 0.75% to 1.5% larger, for example about 1% larger.

The valve stem block may include an annular recess concentric with and extending around the inner bore at least partially around the circumference thereof, the inner diameter of the annular recess being about 25 to 50% larger than the inner diameter of the cylindrical inner bore, for example about 40% larger.

The seal may be inwardly convex.

The seal may have an inner surface which is part of a toroid.

The seal may be located at or near an entrance to the inner bore.

The seal may be formed integrally with, e.g. of the same material as, the material defining the inner bore which may, for example, be moulded plastics.

A further aspect of the present disclosure discloses a breath actuated inhaler having a drive adapted to drive a pressurised canister so as to retract a metering valve stem into the canister to fire the canister, the canister being adapted to move during operation between 1 and 4 mm between end positions of its length of travel relative to the valve stem, the drive being arranged to apply a firing force of between 15N and 60N of force to the canister at a position of the canister relative to the valve stem at which the canister fires.

With this configuration of drive and canister travel, it has been surprisingly found possible to have very accurate and reliable firing of the canister, as well as accurate counting when a dose counter is provided. Furthermore, a long extent of travel of the canister to retract the valve stem can be provided to ensure that both count and fire very reliably occur.

The drive may comprise a drive spring.

The canister may be arranged to move between 1 and 3 mm between the end positions. In one example the movement between the end positions is 3 mm.

The drive may be adapted to provide the firing force as more than 40N, preferably also less than 60N.

The drive may be adapted to provide the firing force as more than 35N.

The firing force may be greater than the sum at the point of firing of opposing forces applied to the canister by a valve stem spring in the canister and a return spring for an actuator pin of a dose counter of the inhaler.

When the present disclosure is implemented in a metered dose inhaler, this may comprise a press and breathe metered dose inhaler, for example in which a canister is pushed by hand to fire, normally directly although indirect operation is an alternative, normally using finger and/or thumb operation of the canister.

BRIEF DESCRIPTION OF THE DRAWINGS

The present invention may be carried out in various ways and a number of preferred embodiments will now be described by way of example with reference to the accompanying drawings, in which:

FIG. 2 shows an exploded view of the inhaler shown in FIGS. 1A and 1B;

DETAILED DESCRIPTION OF THE INVENTION

The following detailed description of embodiments of the inhaler and accompanying methods will be better understood when read in conjunction with the appended drawings of exemplary embodiments. It should be understood, however, that the invention is not limited to the precise arrangements and instrumentalities described in the following detailed description.

Figure 1A:
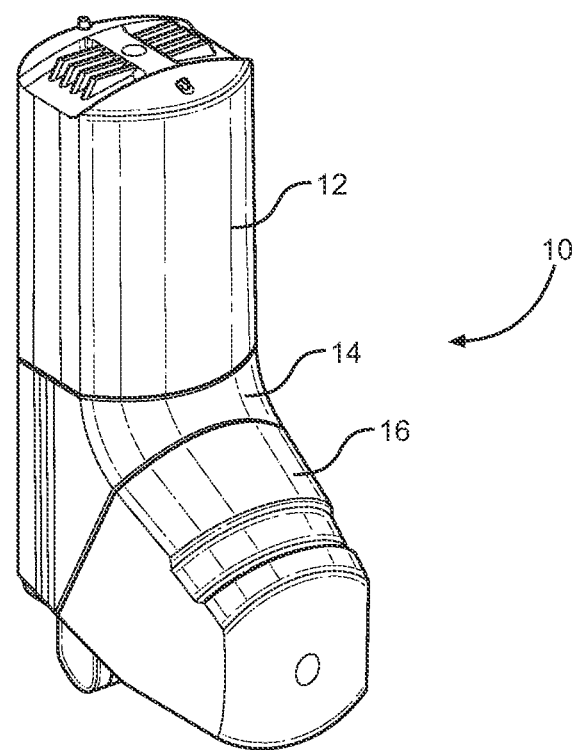
FIGS. 1A and 1B show respective isometric views of a preferred inhaler.
Figure 1B:
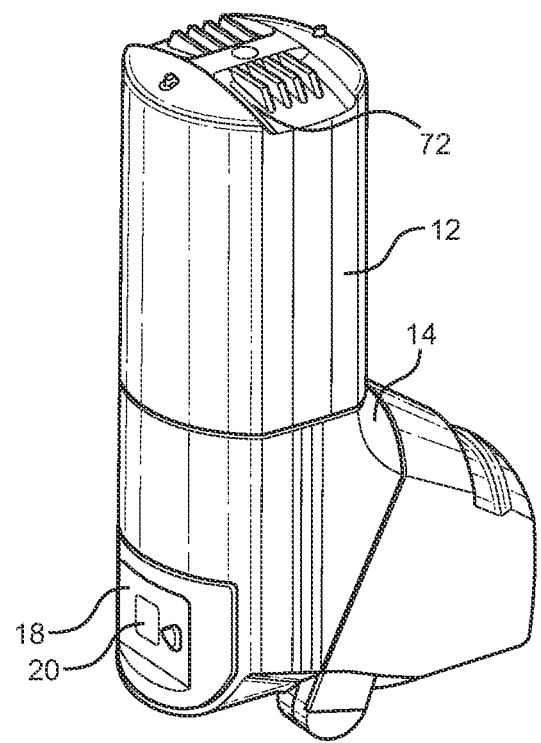

As shown in FIGS. 1A and 1B, a breath actuated inhaler which is merely an example of an inhaler in accordance with the present invention, includes a force holding unit or cap housing 12, a main body 14, a mouthpiece dust cap 16 and a dose counter door 18 having a dose counter window 20.

As shown by the exploded view of FIG. 2, a dose counter chamber 22 includes a dose counter system 24 closed within it by the dose counter door 18.

Figure 3:
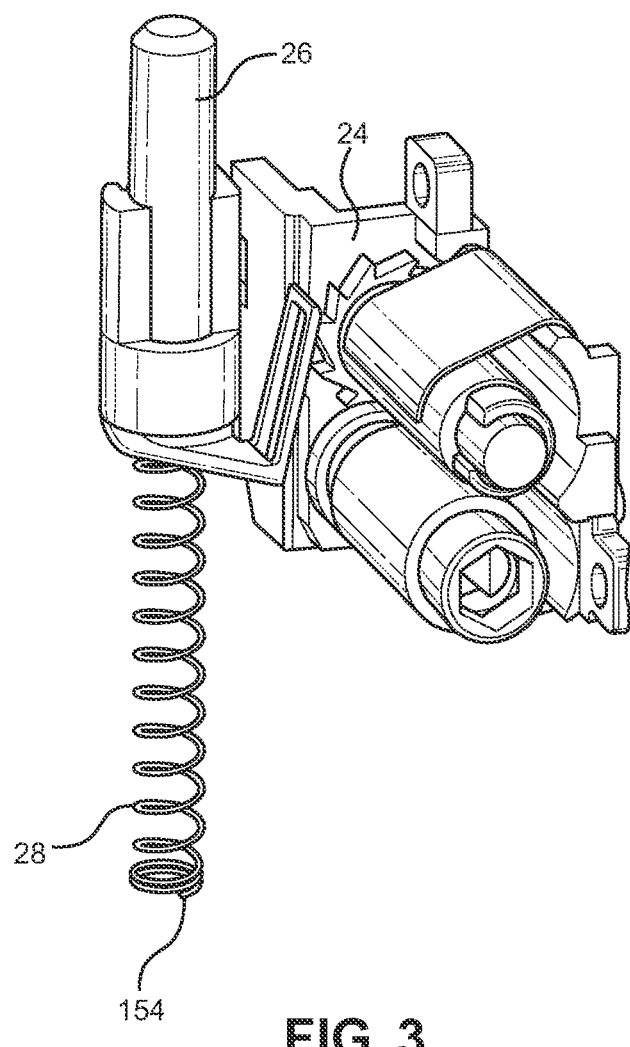
FIG. 3 is an enlarged view of the dose counter assembly shown in FIG. 2.

The dose counter system is shown in enlarged detail in FIG. 3 and includes an actuating pin 26 and return spring 28. The dose counter can take various forms and may, for example, be as described in EP2135199A or EP2514464A.

As also shown in FIG. 2, the inhaler 10 includes a force holding unit 30 which includes: a filter 32, flap valve housing 34, flap valve 36, flap valve spring 38, main compression spring 40, retaining ring 42, diaphragm 44 and lower cap 46. The inhaler also includes a canister 50 with a metering valve 52 and a valve stem 54; as well as a yoke 56 with drive rods or legs 58 having distal ends 59 which are driven by respective cams 60 on the hingedly-connected mouthpiece dust cap. The valve stem 54 is fitted into an inner bore 61 (FIG. 15B) of a valve stem block 62 which communicates with a nozzle 64 for ejection of inhalable substances through a central bore 68 (FIG. 12) of a mouthpiece 66 (FIG. 12 and FIG. 2) of the main body 14 of the inhaler 10.

The force holding unit 30 operates substantially as disclosed with reference to FIGS. 1 to 3 of EP1289589A and the yoke 56 and mouthpiece dust cap 16 substantially as described in EP2514465A, including but not limited to FIG. 22 thereof.

In particular, with reference to FIGS. 5A to 5D, starting from a configuration in which the mouthpiece dust cap 16 is closed in this configuration the liquid 201 in an interior reservoir 84 of canister 50 communicates with a metering chamber 82 which does not communicate with atmosphere through an interior bore 88 of the valve stem 54. An opening rotation of the mouthpiece dust cap 16 to the configuration of FIGS. 6A to 6D enables the distal ends 59 of the drive rods 58 and indeed the whole yoke 56 to be moved away from the cap housing 12 under the influence of the main compression spring 40, the main compression spring 40 being reacted against as equilibrium is reached for the canister position by friction forces as well as forces provided by partial vacuum at the diaphragm, the dose counter return spring 28, and metering valve spring 70 (FIG. 4) which forms part of the metering valve 52. In this configuration, the metering chamber 82 is isolated from both of the interior reservoir 84 and atmosphere.

As the next step, the user (not shown) inhales through the mouthpiece 66 and the drawing out of air through the central bore 68 in turn draws air into the enclosure formed by the main body 14 and cap housing 12 through the series of approximately ten air inlets 72 formed on the cap housing 12. The incoming air impinges upon the flap 74 which releases vacuum (i.e. a partial vacuum) from the vacuum chamber formed by the diaphragm 44 due to flap seal 76 rising off port 78 on diaphragm top plate 80. With the vacuum released, as shown in FIGS. 7A to 7D, as the user is inhaling air through the inhaler 10, i.e. through the apertures 72 and all of the way along inside the cap housing 12 and main body 14 past the canister 50 and out through the central bore 68, the main compression spring 40 drives the lower cap 46, yoke 56 and canister 50 away from the cap housing 12 and towards the main body 14 and valve stem block 62 whereby the valve stem 54 is retracted into the canister 50. This places the pressurised metering chamber 82 in communication with valve stem block nozzle 64 so fires the canister and ejects inhalable substances from the metering chamber 82 through the nozzle 64 and mouthpiece 66 towards the lungs (not shown) of the user. The dose counter system 24 also registers a count by movement of the actuating pin 26 by the canister ferrule 220. At this time after opening and firing, the metering chamber 82 communicates with atmosphere. With the mouthpiece 66 left open such that the atmosphere communicates through the bore 88 and exit port 90 with the metering chamber 82, the metering chamber 82 can become at least partially or fully filled with gas such as air from the atmosphere.

In other embodiments comprising nasal inhalers, the mouthpiece 66 may be replaced with a nose piece.

As shown in FIGS. 8A to 8D, during closing, the mouthpiece dust cap 16 is rotated back to its closed position and the cams 60 push on the distal ends 59 of the drive rods 58 so as to push the yoke 56 towards the cap housing 12 so as to compress the main compression spring 40 again and the vacuum is formed again at the diaphragm 44. At the same time, the canister is pushed back to its original configuration of FIGS. 5A to 5D by the metering valve return spring 70.

Figure 9:
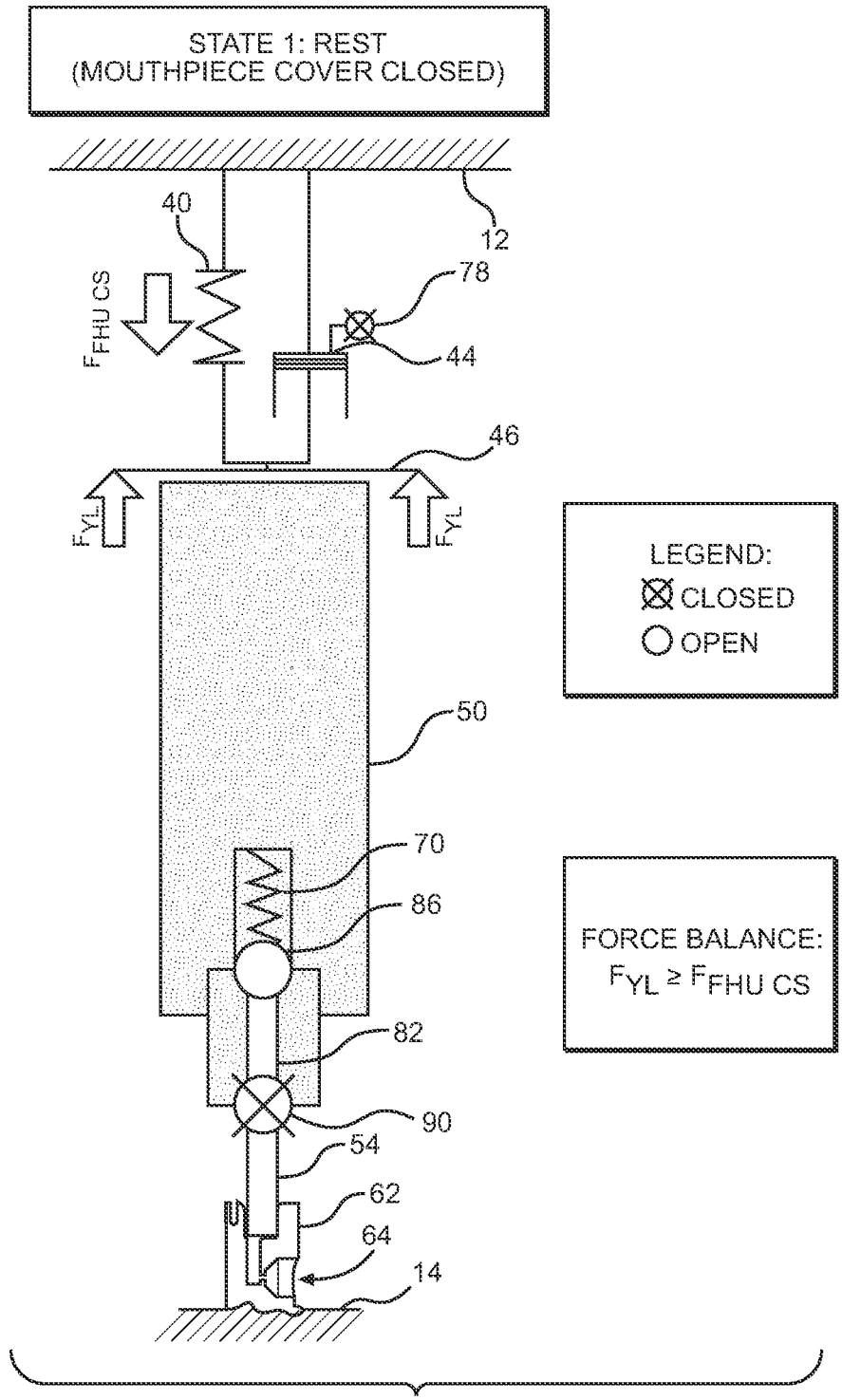
FIG. 9 schematically shows forces and ports within the inhaler in the closed configuration of FIGS. 5A to 5D.

As shown in FIG. 9, with the inhaler 10 in the configuration of FIGS. 5A to 5D, the metering valve spring 70 keeps the valve stem 54 extended, the inlet port 86 open and the exit port 90 effectively closed, i.e. with the metering chamber 82 isolated from atmosphere. At the same time the force $F_{YL}$ applied as $F_{YL}/2$ by each of the legs or rods 58 of the yoke 56 to the lower cap 46 is greater than or equal to the force $F_{FHUCS}$ applied in the opposite direction by the spring of the force holding unit 12.

Figure 10:
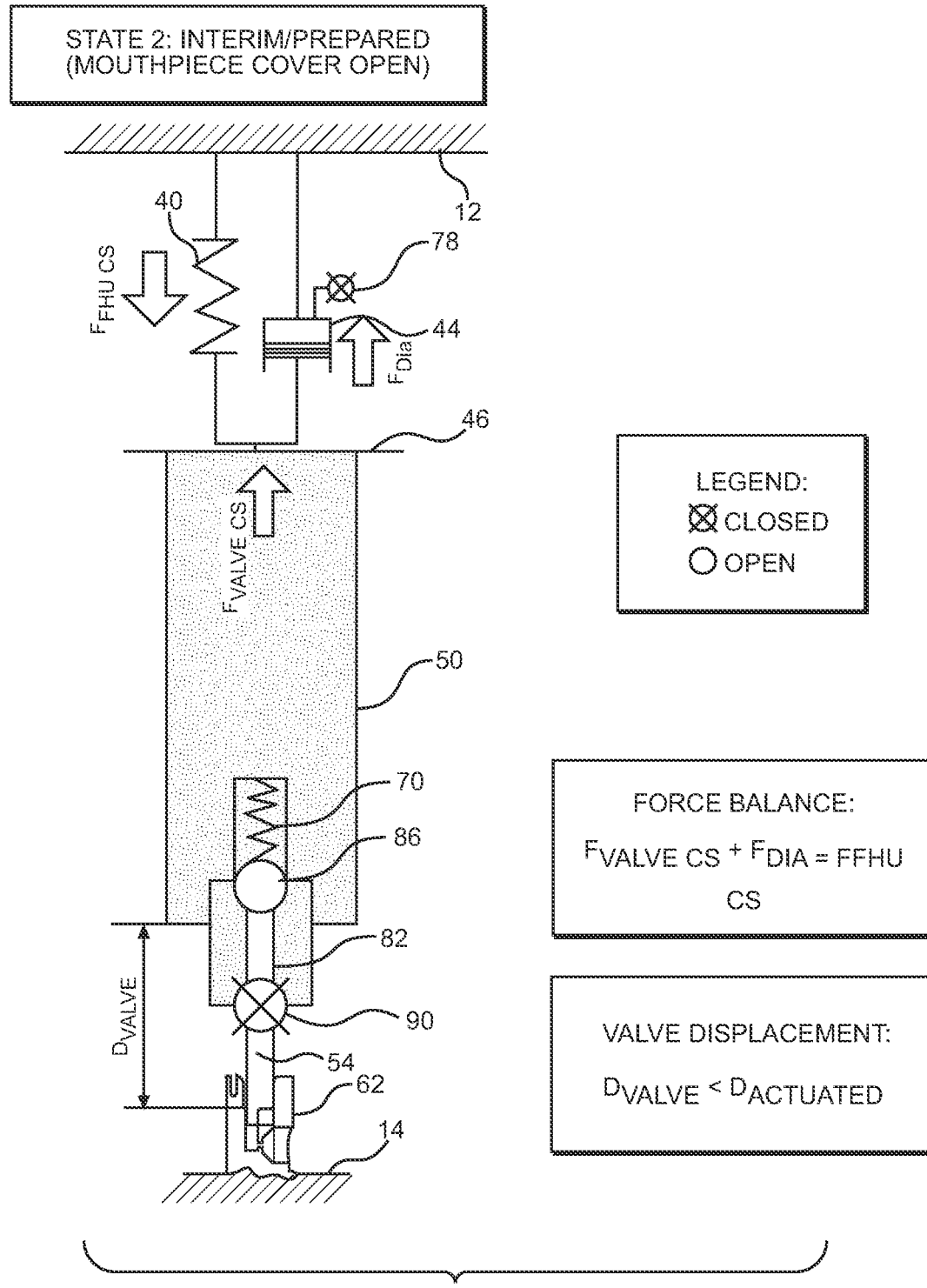
FIG. 10 schematically shows forces and ports within the inhaler in the opened configuration of FIGS. 6A to 6D.

As shown in FIG. 10, with the inhaler then changed to the configuration of FIGS. 6A to 6D, the canister is displaced to a representative distance $D_{valve}$ from the canister position of FIG. 9 where this displacement at $D_{valve}$ is less than the displacement required to actuate and fire a dose. In this FIG.

10 configuration, the position of the canister 50 is determined by an equilibrium between forces, which is:

$$F_{valve\ CS} + F_{Dia} = F_{FHU\ CS}$$

where $F_{valve\ CS}$ is the force applied to the canister by the metering valve spring 70, $F_{Dia}$ is the force applied by the partial vacuum in the diaphragm 44 in the same direction and $F_{FHU\ CS}$ is the opposing force applied by the compression spring 40 of the force holding unit 30. The port 78 is noted to be closed. The port 86 is open and the port 90 is closed.

Figure 11:
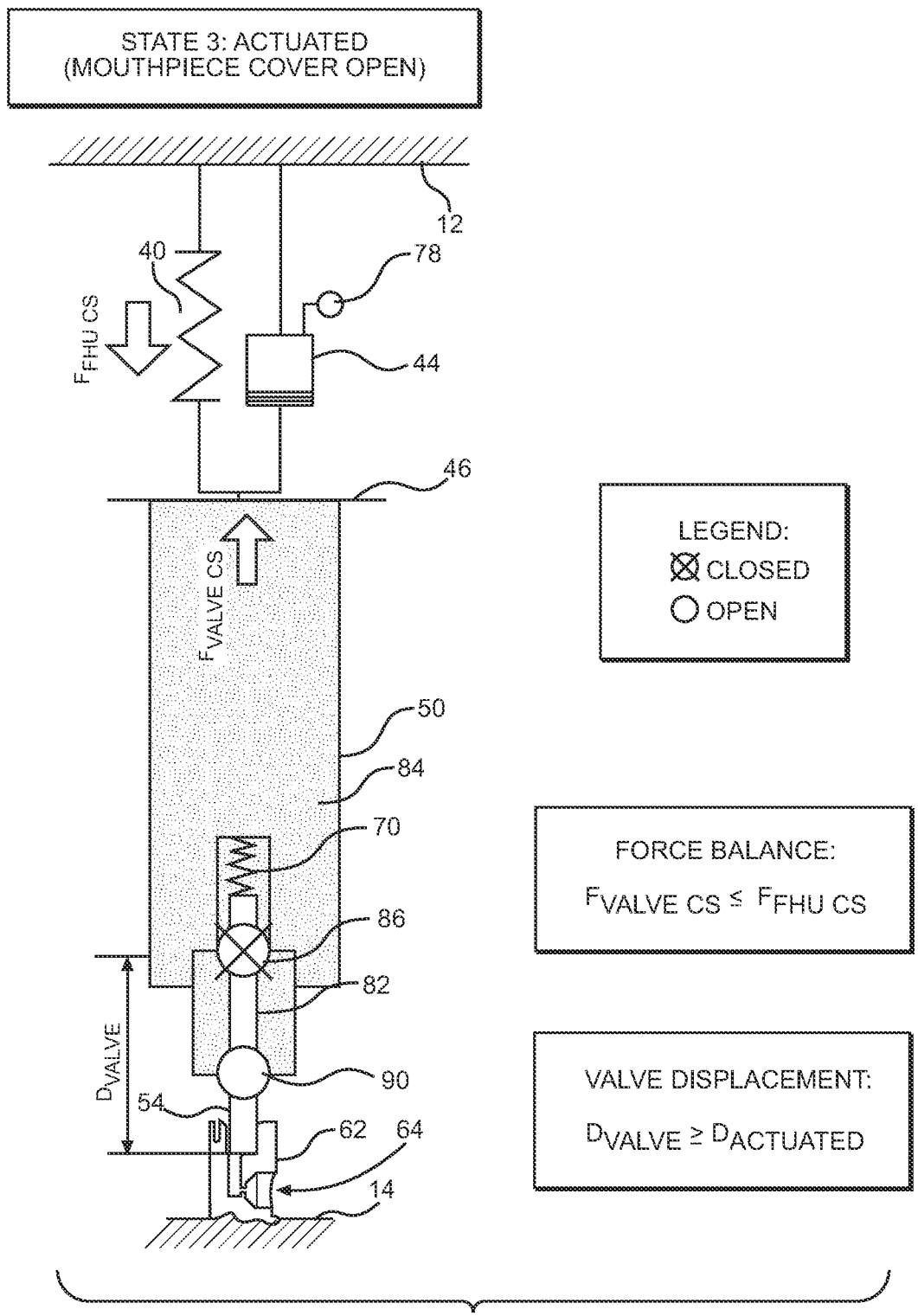
FIG. 11 schematically shows forces and ports within the inhaler in the actuated configuration of FIGS. 7A to 7D.

As the user then inhales, the port 78 is opened by the action of air entering through the apertures 72 impinging on the flap 74, lifting flap seal 76. The equilibrium of FIG. 10 is therefore lost. The canister 50 is therefore moved to displace the valve stem 54 more, to the configuration of FIG. 11, so that the canister is a representative distance $D_{Actuated}$ from the valve stem block 62, and where the force balance is that $F_{valve\ CD} \leq F_{FHUCS}$ in which the force applied to the lower cap 46 is less than or equal to the opposing force applied by the compression spring 40 of the force holding unit R. In this configuration, the port 86 has closed to isolate the metering chamber 82 from the interior reservoir 84 of the canister 50 and after this closure the port 90 has opened, thereby firing the canister 50 by venting pressurised contents within the metering chamber 82 out through the nozzle 64 of the valve stem block 62 for inhalation by the user.

The spring 40 is adapted such that the firing force $F_{FHU\ CS}$ is more than 35 N, typically less than 60 N. This may vary in other embodiments.

In most embodiments, the spring 40 is adapted in addition to device geometry such that the force exerted by the spring 40 on the valve/canister is equal to the sum of the opposing valve spring 70 and pneumatic resistance force in the FHU diaphragm 44 in the prepared position. Nonetheless, the spring 40, unless otherwise assisted, must be able to provide sufficient force once the mechanism is triggered to actuate the canister on inhalation. The specific force values will be dependent on the componentry of the device, driven predominately by the force required to actuate the canister at a specific displacement, thus the spring 40 will be adapted to suit.

Figure 4:
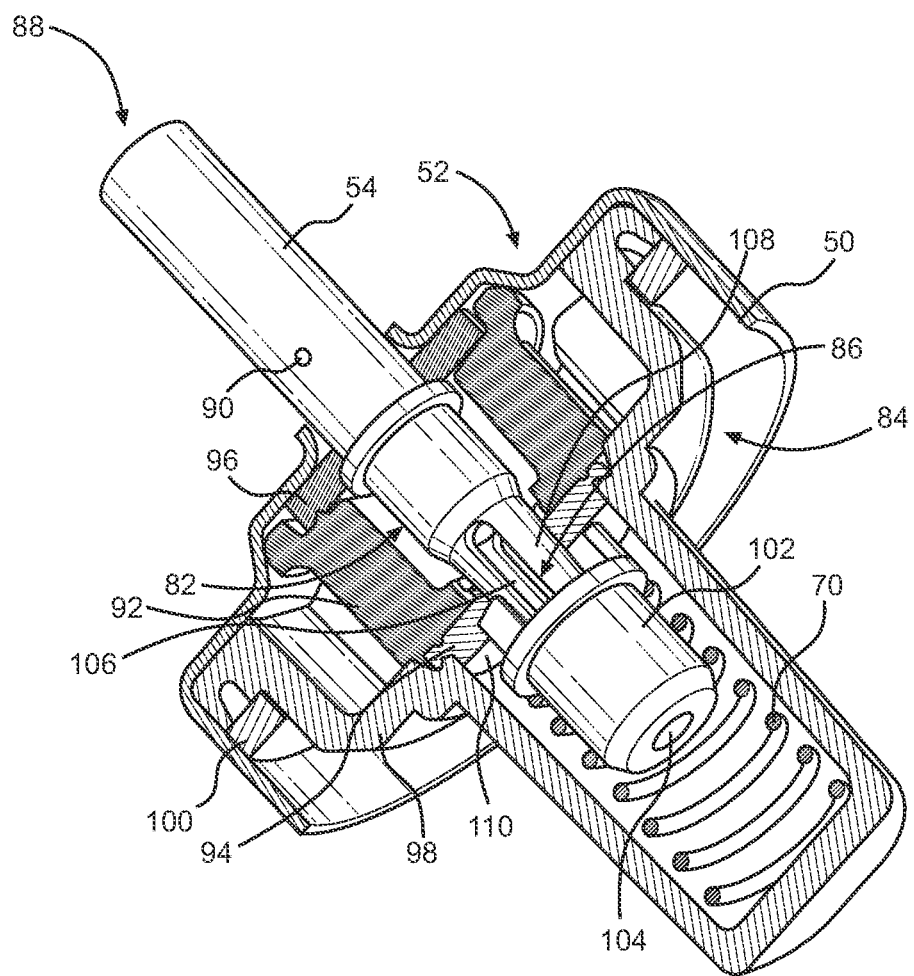
FIG. 4 is an isometric sectional view of a metering valve of the inhaler and part of the canister shown in FIG. 2.
Figure 5A:
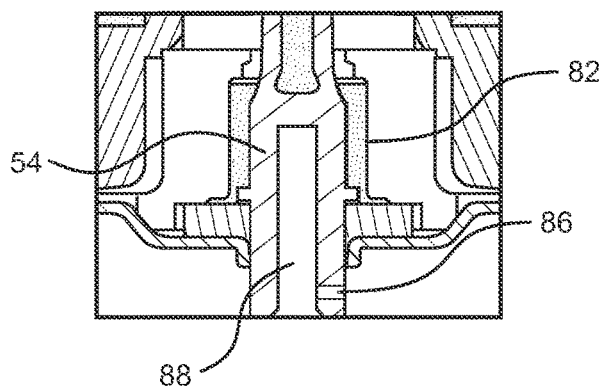
FIGS. 5A, 5B, 5C and 5D show various details of the inhaler and parts of it in a closed configuration thereof.
Figure 5B:
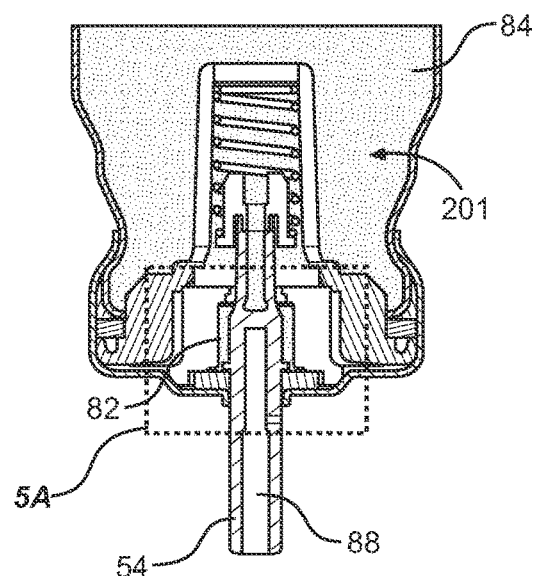
Figure 5C:
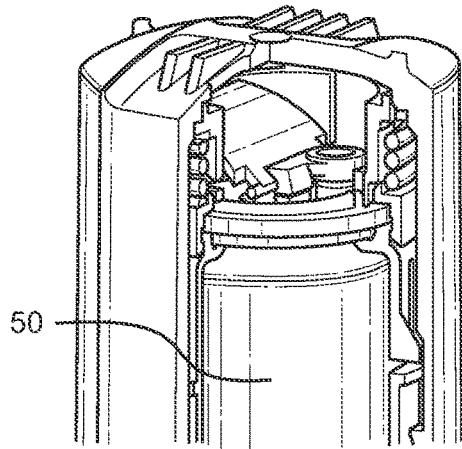
Figure 5D:
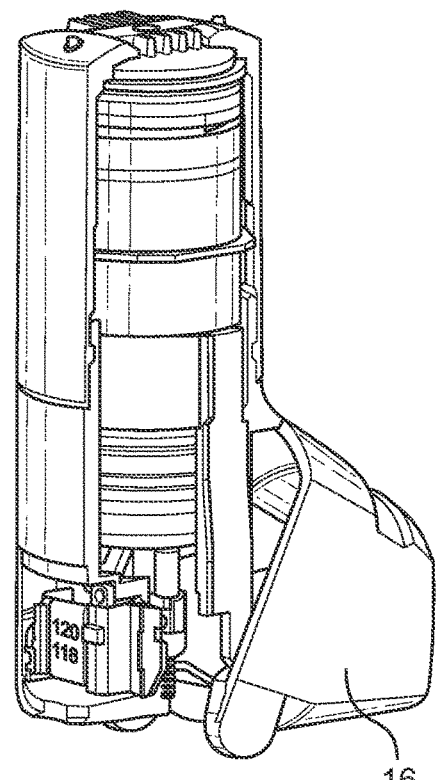
Figure 6A:
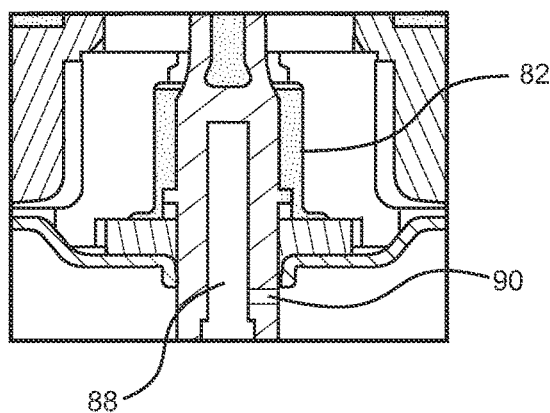
FIGS. 6A, 6B, 6C and 6D show various details of the inhaler in an opened configuration thereof.
Figure 6B:
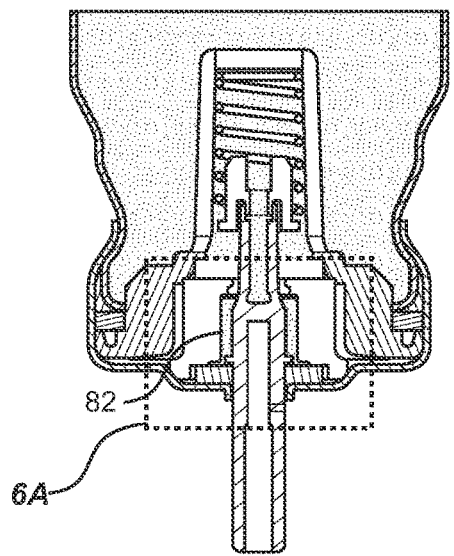
Figure 6C:
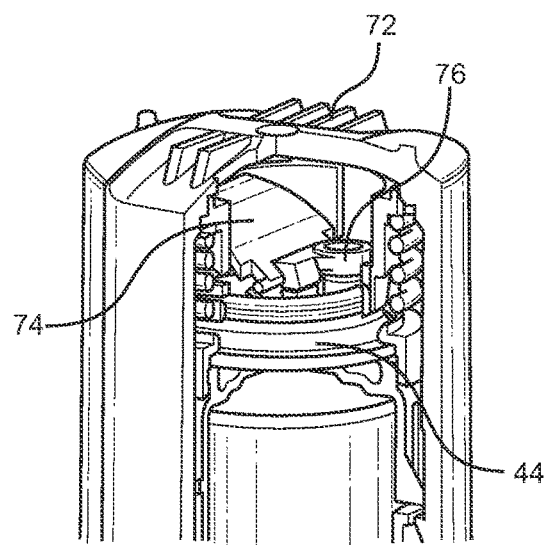
Figure 6D:
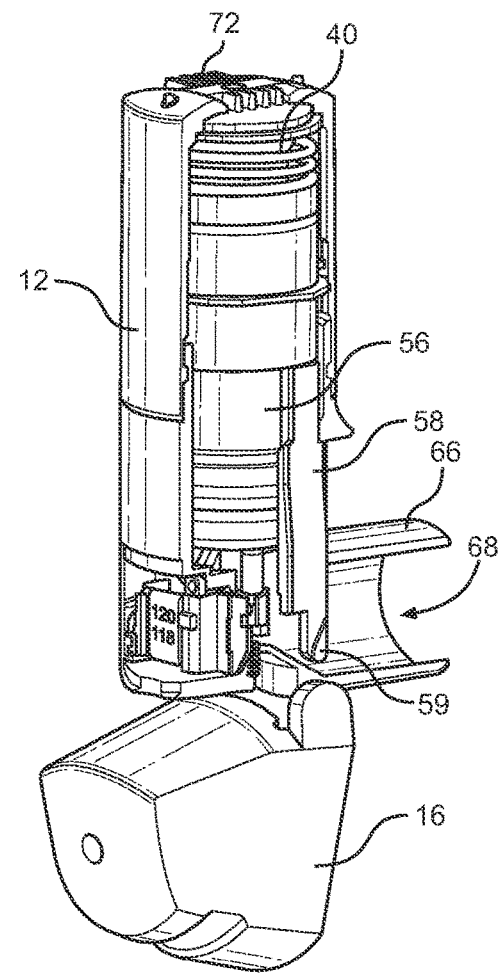
Figure 7A:
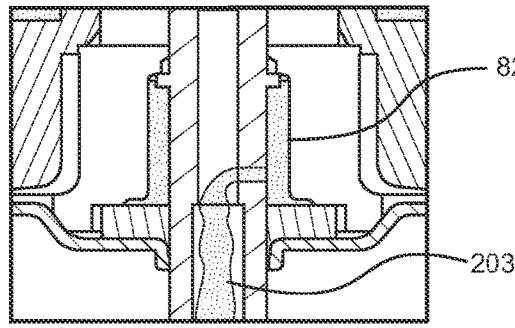
FIGS. 7A, 7B, 7C and 7D show various details of the inhaler in an actuated configuration thereof.
Figure 7B:
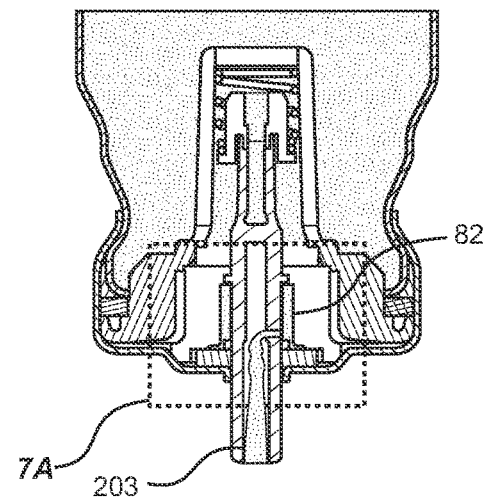
Figure 7C:
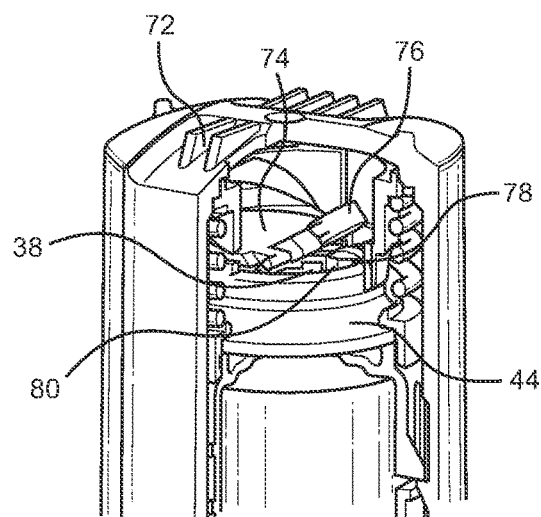
Figure 7D:
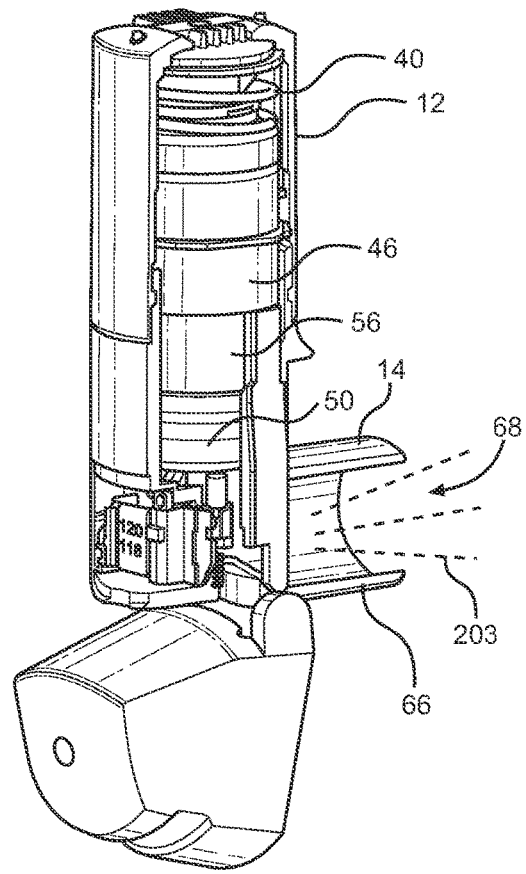
Figure 8A:
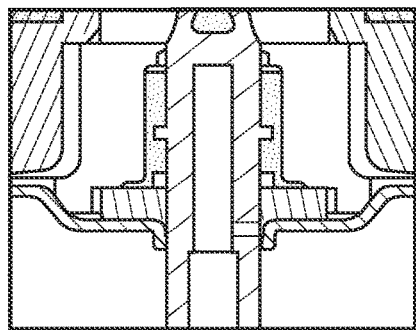
FIGS. 8A, 8B, 8C and 8D show various details of the inhaler in a closing configuration thereof.
Figure 8B:
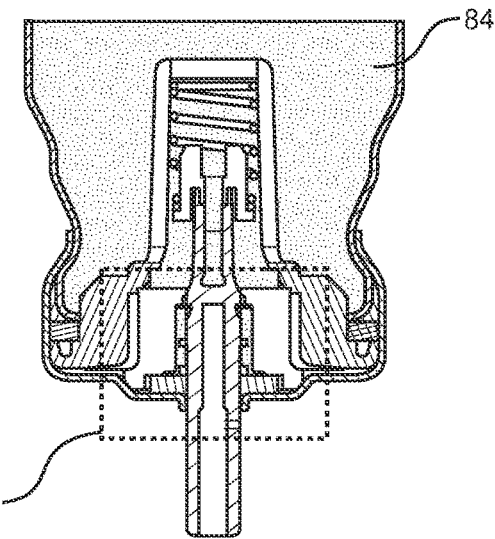
Figure 8C:
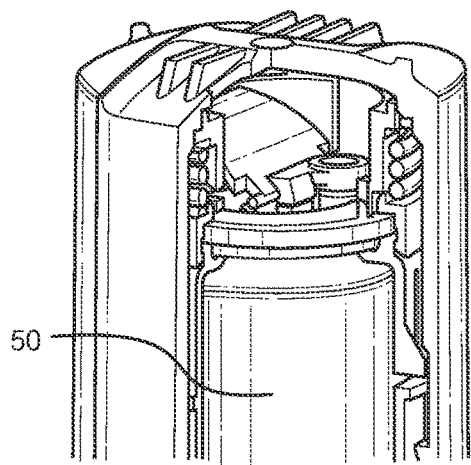
Figure 8D:
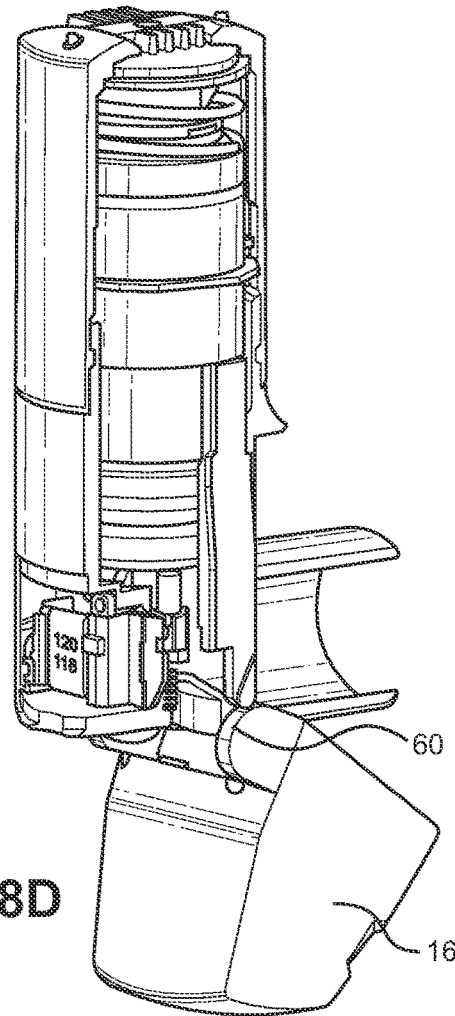

The metering valve 52 shown in FIG. 4 is similar to those described in U.S. Pat. No. 7,959,042B, which is incorporated by reference herein, and has the metering chamber 82 arranged for selective communication with either the interior reservoir 84 of the canister 50 via an inlet port 86, or with the interior bore 88 (FIGS. 5A to 5D) of the valve stem 54 which communicates via the valve stem block 62 with the nozzle 64, the valve stem 54 being provided with a radially configured capillary exit port 90 leading to the bore 88. The metering chamber 82 is at least partly defined by a cup-shaped inner metering body 92 and has an inner seal 94 and outer seal 96, as well as a location member 98, a main canister seal 100 and a crenelated valve stem driver 102 which has a through bore 104 axially directed towards the inlet port 86. The inlet port 86 includes two elongate openings 106 diametrically opposed to one another and which are defined by a pair of forked legs 108 which are spaced apart from one another by the elongated openings 106 and the open space forming the inlet port 86 between them. The forked legs 108 have substantially constant cross-section all the way along to their distal ends (not shown) which are located within the crenelated valve stem driver 102.

When the valve stem 54 is depressed into the canister 50 so that the inlet port 86 permits communication between the metering chamber 82 and the interior reservoir 84, the communication into the interior reservoir 84 is at an inner side 110 of the inner seal 94 and it will be appreciated that this is a slot-shaped porting between the forked legs 108 from where flow can travel directly axially into or out of the interior reservoir 84.

According to an alternative embodiment, the arrangement of openings in the metering valve of the present invention is similar to those described in US2016/0084385, which is incorporated by reference herein. In particular, the metering valve of the present invention may be similar to the embodiment shown in FIG. 4 of US2016/0084385, in which the valve body includes at least one first opening (i.e., at least one first side hole 100 that is arranged in a cylindrical portion of the valve body) and at least one second opening (i.e., at least one second hole 111 that, as with the first hole(s), is arranged in a cylindrical portion of the valve body), the second opening(s) being axially offset relative to the first opening(s) along a longitudinal axis that extends between a first axial end and a second axial end of the valve body. The first opening(s) and second opening(s) that are axially offset from each other along the valve body enable the metering chamber to be filled and emptied.

The canister 50 includes inhalable substances including the active ingredient beclomethasone dipropionate and the propellant HFA134a which has a surface tension of about 8 mN/m as liquid at 25° C. Other active ingredients may be used in other embodiments, such as tiotropium bromide.

If the mouthpiece dust cap 16 is left open such that the atmosphere communicates through the bore 88 and exit port 90 with the metering chamber 82, the metering chamber can become at least partly or substantially fully filled with gas such as air from the atmosphere. When the mouthpiece dust cap 16 is closed, however, and when the interior reservoir 84 is oriented above the metering chamber 82, the present inventors have discovered that the liquid phase in the interior chamber can exchange places with gas in the metering chamber 82, the fluid travelling either directly through the openings 106 or through the throughbore 104, and along through the inner seal 94 and into the metering chamber 82 and gas in the metering chamber 82 can travel in the reverse direction along the same path, exiting with an axial component through between the forked legs 108 and through the elongated openings 106 into the interior reservoir 84. It is believed that the particular surface tension of the chosen propellant promotes this action and the higher density of the liquid than that of any gas in the metering chamber enabling the latter to rise up in and relative to the liquid.

The full filling of the metering chamber 82 with a dose of liquid from the interior reservoir 84 with any gas in the metering chamber passing in the reverse direction from the metering chamber 82 into the interior reservoir 84 is highly advantageous since with this one extension of the valve stem 54 from its retracted configuration after inhalation to its extended configuration with the mouthpiece dust cap 16 closed again ensures that the inhaler 10 is fully primed for use. This has overcome a significant problem.

Figure 20:
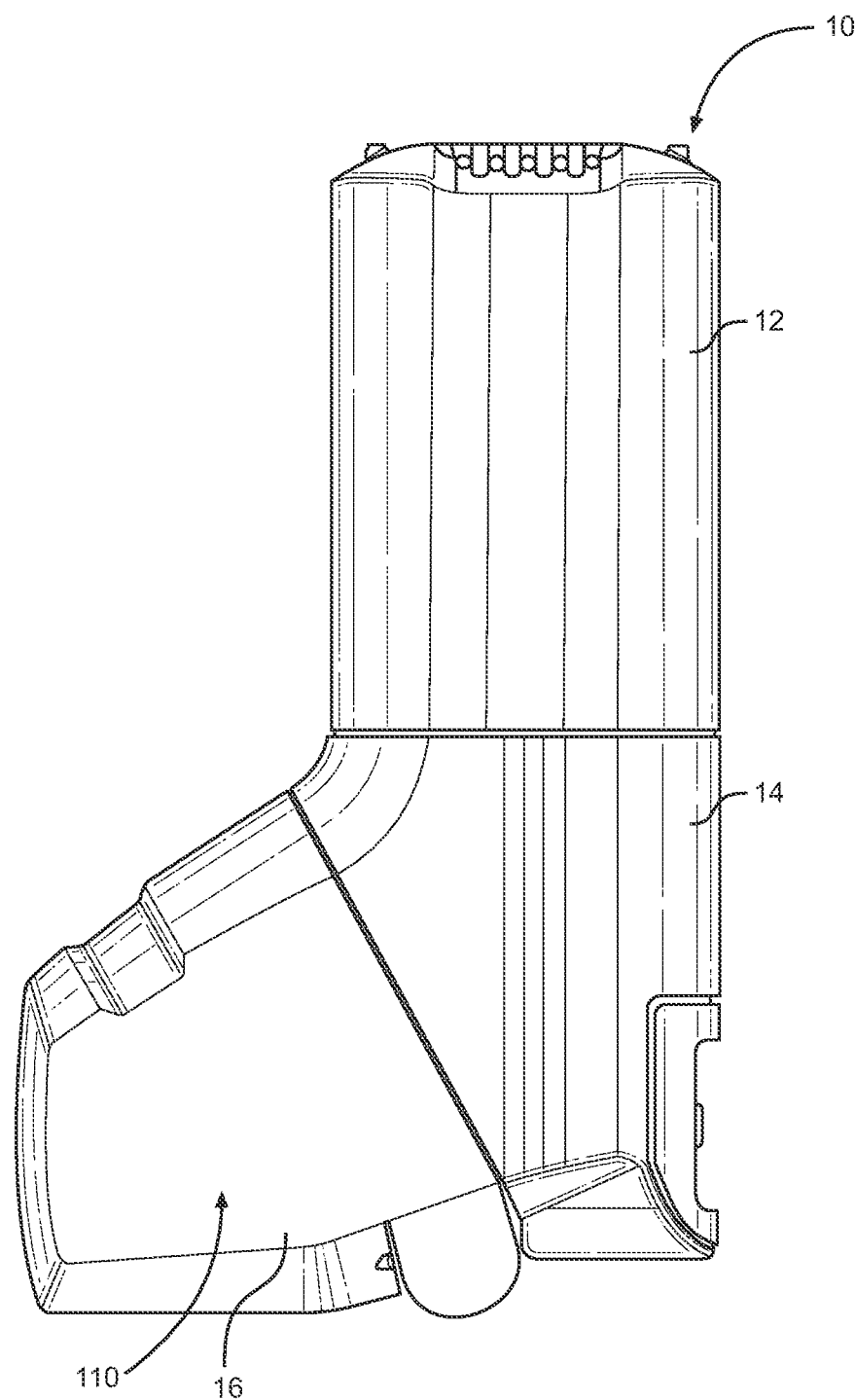
FIG. 20 shows a side view of the inhaler shown in FIG. 1A.

As shown in FIG. 20, the inhaler 10 may be provided with a preventer 110 for preventing the user from taking a second or further inhalation while the dust cap 16 is still open. The preventer 110 may take the form of a warning signaller 102 such as a warning notice as shown in the drawing stating "to reload: close before each inhalation" although in other embodiments the preventer 110 could take various other forms such as an alarm or audible or visual warning device to indicate that the mouthpiece dust cap 16 is open and needs to be closed prior to the next inhalation.

Figure 21:
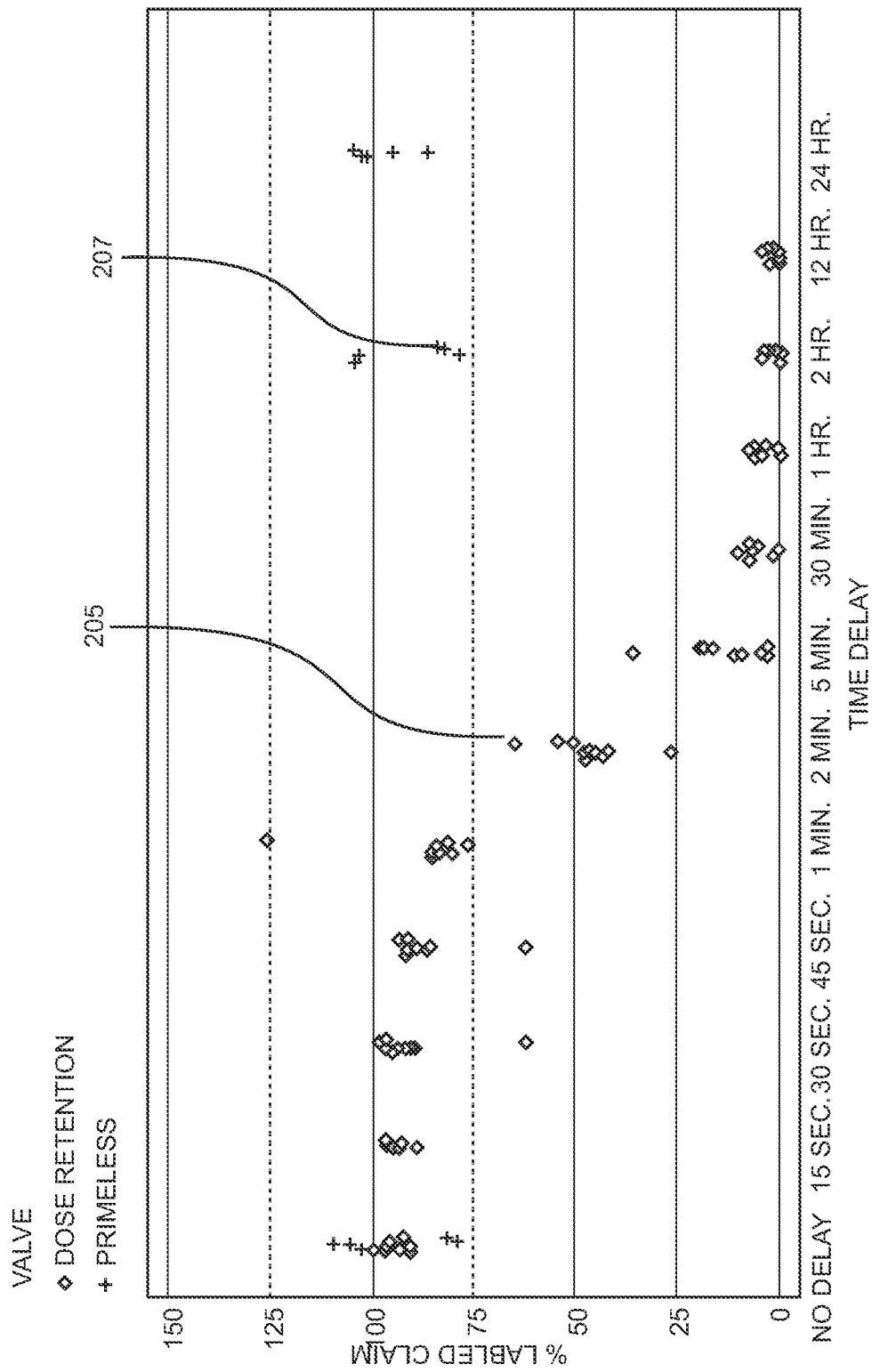
FIG. 21 shows a comparative graph of delivered dose recovery at various time delays post previous actuation for the inhaler of FIG. 1A and an inhaler having a metering valve with radial capillary metering chamber inlet and outlet ports.

FIG. 21 is a graph showing a comparison of the inhaler of FIG. 1A with delivered dose for a prior art breath actuated inhaler with a different metering valve (not shown) in which the exit port from the interior reservoir comprises a radially oriented capillary bore which leads to an internal bore of the valve stem leading axially towards a further radially extending capillary port, such that the communication from the interior space is through the first capillary port, along the internal bore and out through the second radial capillary port into the metering chamber when the valve stem is in its extended configuration. In all cases the inhalers were held with the valve stems vertical and the canister interior reservoir above the metering chamber. After inhalation, the valve stem in each case was left in the retracted inhale configuration with the metering chamber exposed to atmosphere through the valve stem for the specified delay period and the inhaler was then reset and readied for inhalation, in the case of the present inhaler 10 by closing and opening the mouthpiece cap again. As shown by the graph of FIG. 21, with a target of 80 micrograms of BDP (beclomethasone dipropionate) the diamond shaped plots 205 are for the prior art inhaler which began to fail to reach 75% of the labelled claim for the dose after a delay of 30 seconds after inhalation in closing the mouthpiece cap to isolate the metering chamber from atmosphere. At all delays of 2 minutes or over, the prior inhaler failed to provide 75% of the labelled claim of dose in 100% of cases. This, the present inventors have discovered, is due to gas lock forming in the metering chamber after inhalation due to the metering chamber's exposure to atmosphere, i.e. in that when the mouthpiece cap is closed after a delay air is trapped in the metering chamber and is not replaced by liquid in the interior reservoir even when the metering chamber is connected to the interior reservoir. In contrast, the plots of crosses 207 in FIG. 21 show the performance of the inhaler of FIG. 1A. Here, 100% of the plots are in the range of 75 to 125% of labelled claim for the dose, even when there is no appreciable delay or a delay of one hour, twelve or twenty-four hours before closing the mouthpiece cap after inhalation.

Therefore, even if the metering chamber 82 has been exposed to atmosphere for a relatively long time such that it is after that delay substantially full of gas due to evaporation/diffusion of substances after inhalation, this graph clearly shows that by closing the mouthpiece fully and opening it again, the gas in the metering chamber 82 is removed into the interior reservoir 84 and replaced with a correct dose very reliably.

Although FIG. 21 data is presented for 80 mcg (ex-actuator) targeted BDP HFA product, the data is representative of any formulation and formulation strength.

Figure 12:
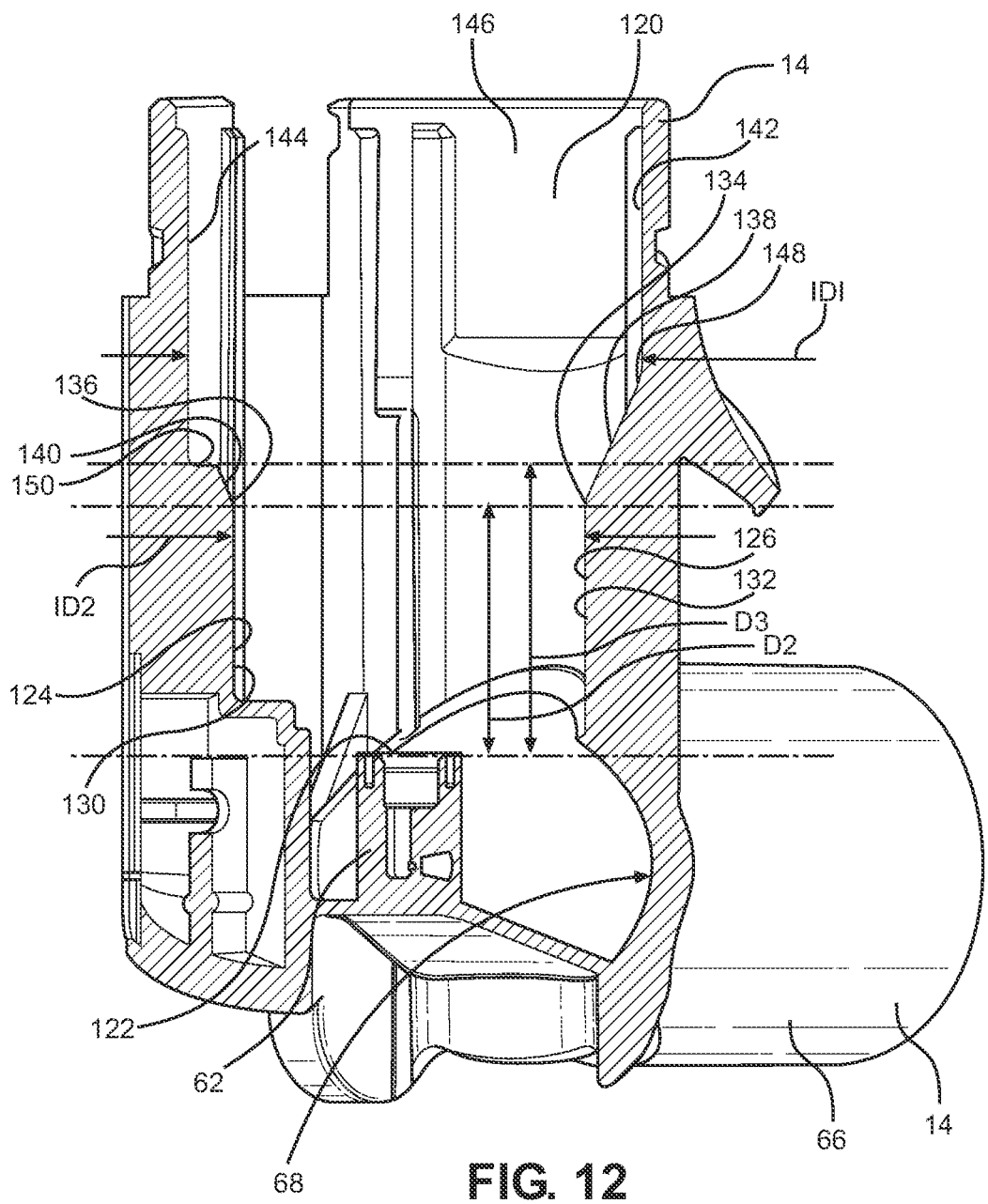
FIG. 12 is a sectional elevational view of part of the inhaler shown in FIG. 1A with long dash lines denoting the top of ribs used in an earlier prototype.

As shown in FIG. 12, the main body 14 has a tubular body portion 120 arranged to contain the pressurised canister 50 for sliding motion. As shown in FIG. 12, the valve stem block has a top surface 122 and the tubular body portion 120 has at least two mutually opposed guide ribs 124, 126. The guide ribs 124, 126 have substantially straight guide edges 130, 132 extending parallel to and spaced from one another, each straight guide edge 130, 132 having an upper corner 134, 136 where the straight guide edge meets a further surface 138, 140 of the ribs 124, 126 leading outwardly towards an upper rib section near an inner wall 146 of the tubular body portion 120. At least one of the ribs 124, 126 has its straight guide edge's upper corner 134, 136 positioned a distance D2 in a direction parallel to an axis of the valve stem block 62 along away from the top surface 122 of the valve stem block 62, a distance between the straight guide edges 130, 132 of the ribs 124, 126 perpendicular to the axis being ID2, and the ratio D2 divided by ID2 is 0.7. This is smaller than in previous embodiments and can surprisingly assist in providing smooth guiding of the canister within the tubular body portion 120.

The further surface 138, 140 of at least one of the guide ribs 124, 126 and in this case both of them extends away from the valve stem block 62 and terminates at a distance D3—in the case of guide rib 124—from the top surface 122 of the valve stem block 62 in the direction parallel to the axis, the ratio D3 divided by ID2 being 0.8, the equivalent ratio for the guide rib 126 being 1.0. Each guide rib meets the upper rib section 142, 144 near the inner wall 146 of the tubular body portion 120 at an outer rib position 148, 150 wherein the outer rib positions are a distance apart ID1 in a direction perpendicular to the axis 202 of the valve stem block 62 and the ratio ID2 divided by ID1 is 0.8. This arrangement assists beneficially in providing sufficient space for the canister 50 to move within the tubular body section 120.

Figure 13:
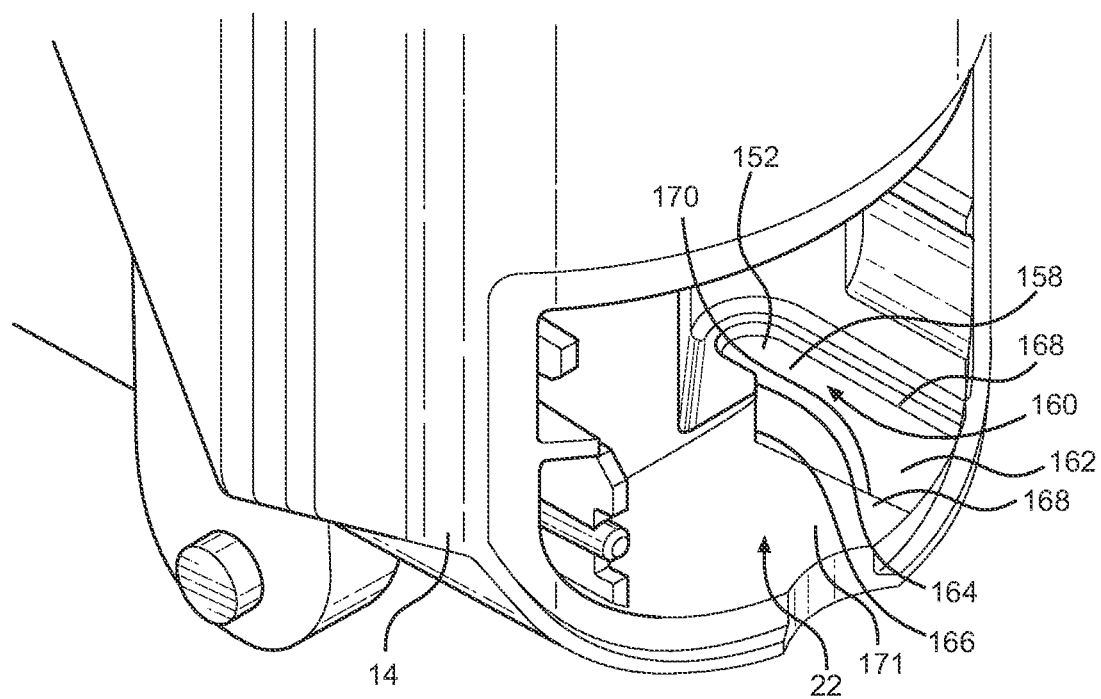
FIG. 13 shows a portion of the inhaler of FIG. 1A with the dose counter and dose counter door removed.

With reference to FIG. 13, a portion of the main body 16 is shown with the mouthpiece dust cap 16 and the dose counter door 18 and the dose counter system 24 not yet installed. As can be seen, the dose counter chamber 22 includes a recess 152 for location of an end 154 (FIG. 3) of the return spring 28. The recess 152 has a substantially flat reaction surface for pushing on the end 154 of the return spring 28. The recess 152 also has a shoulder surface 158 adjacent the reaction surface 156 and an entrance mouth 160 into the reaction surface 156. A distinct guide surface 162, which is substantially planar is provided for guiding the end 154 of the return spring 28 into the recess 152 during assembly. The distinct guide surface 162 is wider than the entrance mouth 160 in a direction across the mouth and this assists substantially in assembling the spring 28 into the recess 152.

The entrance mouth 160 also has at least a chamfered entrance lip 164, an extension 166 of which into the guide surface forms a slanted edge 166 of the distinct guide surface 162.

At least a portion of the distinct guide surface 162 comprises a portion of the body 14 which is recessed relative to the adjacent and partially surrounding portion 164 of the body by an edge 168. The edge 168 is particularly effective in catching the end 154 of the return spring and the wide guide surface 162 is effective in guiding the spring 28 past the chamfered entrance lip 164 and onto the reaction surface 156 where it remains once installed. A further edge 170 of the guide surface 162 is spaced from and generally parallel to the edge 168. The edge 170 forms an intersection with an adjacent portion 171 of the body 14.

Figure 14A:
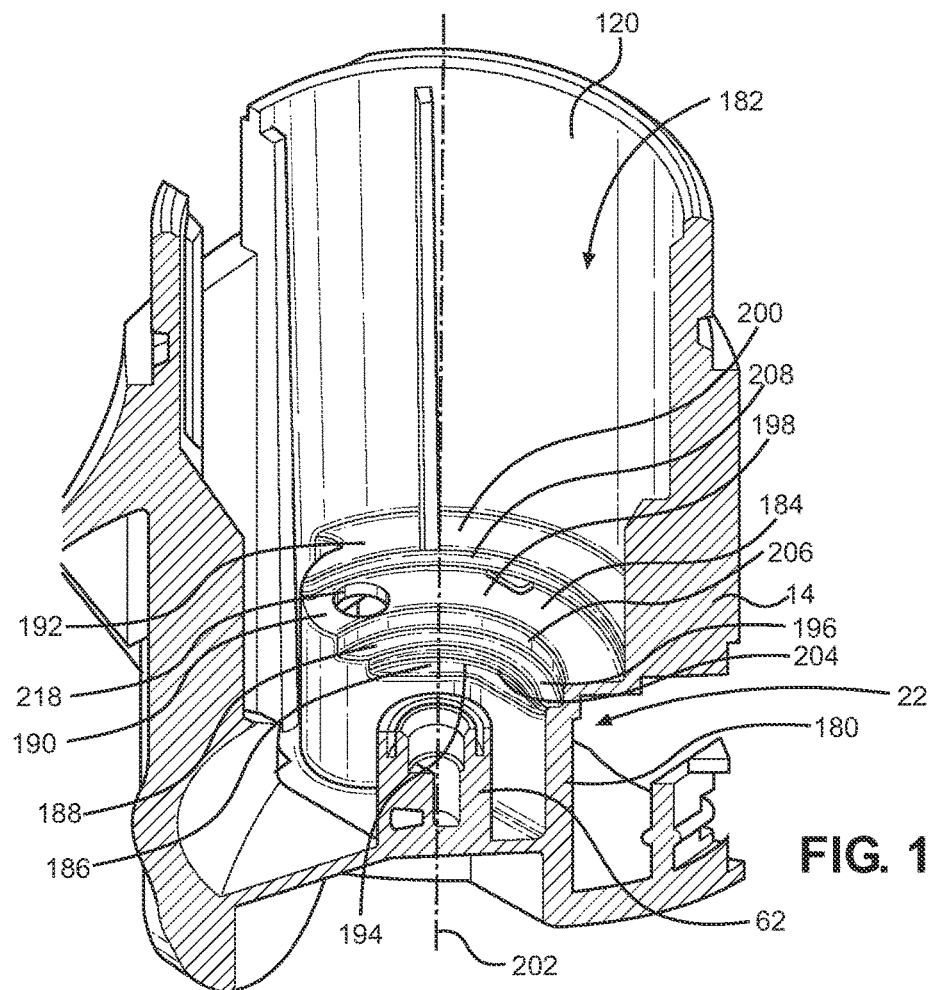
FIG. 14A is a sectional isometric view of part of the inhaler shown in FIG. 1A.

As shown in FIG. 14A, the main body of the inhaler 10 includes a barrier 180 separating an interior space 182 defined at least partly by the tubular body portion 120 from the dose counter chamber 22. The barrier includes a stepped upper wall area 184 which has four steps 186, 188, 190, 192 at different levels. The steps are arcuate and have substantially flat parts 194, 196, 198, 200 aligned substantially perpendicular to the axis 202 of the valve stem block as well a part-cylindrical risers 204, 206, 208 between the substantially flat parts 194, 196, 198, 200.

The arcuate steps 186, 188, 190, 192 are substantially concentric with the axis 202 of the valve stem block 62. The steps 186, 188, 190, 192 extend around the valve block 62 a distance/angle of about 170° although this is only approximate and may be in the region of about 180 to 120° in various embodiments. The material forming the barrier 180 is of substantially constant thickness throughout the steps 186, 188, 190, 192 which is advantageous for manufacturing techniques by moulding.

Figure 14B:
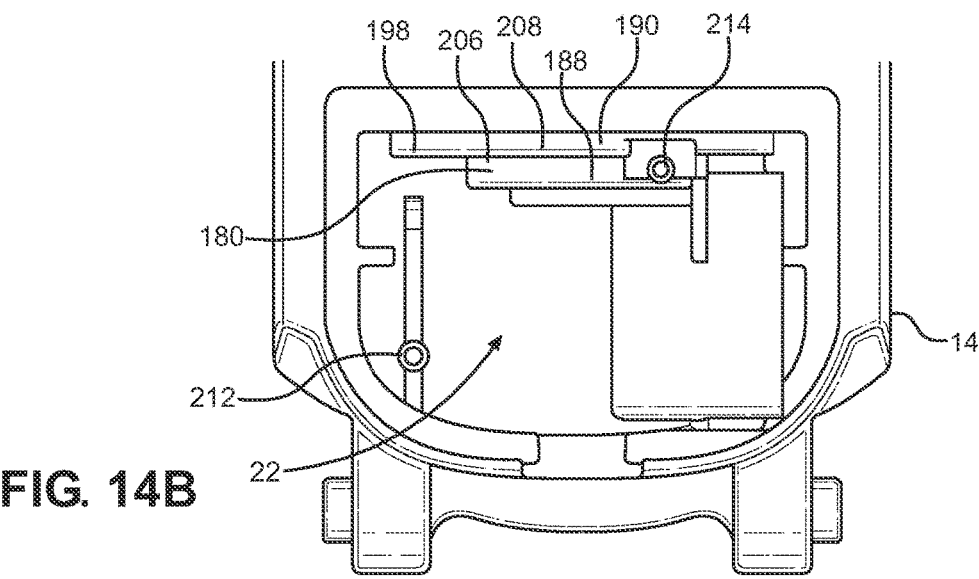
FIG. 14B shows part of the inhaler with a dose counter not yet installed, showing heat stake pins.

As shown in FIG. 14B which is a view into the dose counter chamber 22, the dose counter chamber 22 is formed with two heat staking pins 212, 214 for attaching the dose counter system 24 permanently into position within the dose counter chamber 22. One of the heat staking pins 214 is directly attached to two of the steps 188, 190. The heat staking pin 214 is attached to one substantially flat step part 198 and to two step risers 206, 208, providing secure and advantageous location of the heat staking pin 214 in the stepped upper wall area 184 of the barrier 180. An aperture 218 for the actuating pin 26 of the dose counter system 24 is formed through the second furthest step part 198 away from the valve stem block 62.

The stepped upper wall area 184 is highly advantageous since it enables the accommodation of a length of movement of the canister 50 and in particular its ferrule 220 (FIG. 2) within the main body 14. Therefore, even with a metering valve 70 as used in the inhaler 10 which has a relatively long end-to-end travel of approximately 4 mm, the internal components can be maintained within a relatively small and compact inhaler 10, while also allowing for space in the dose counter chamber 22 for the dose counter system 24 and enabling the dose counter to be heat staked firmly in place by the heat stake pins 212, 214 including the pin 214 which is attached to the stepped upper wall area 84 of the barrier 180.

Figure 15A:
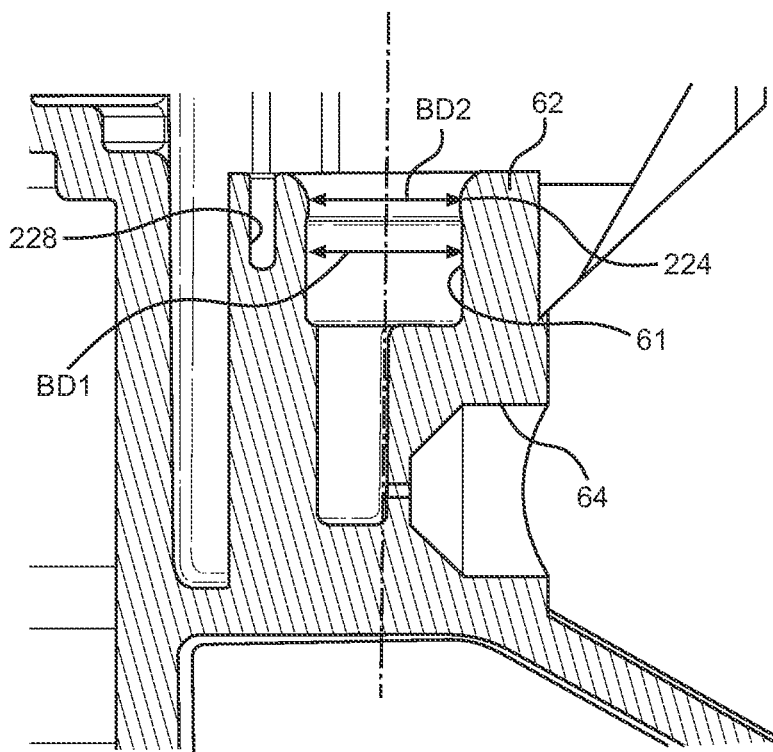
FIGS. 15A and 15B show respective side elevation and isometric views of the valve stem block of the inhaler of FIG. 1A.
Figure 15B:
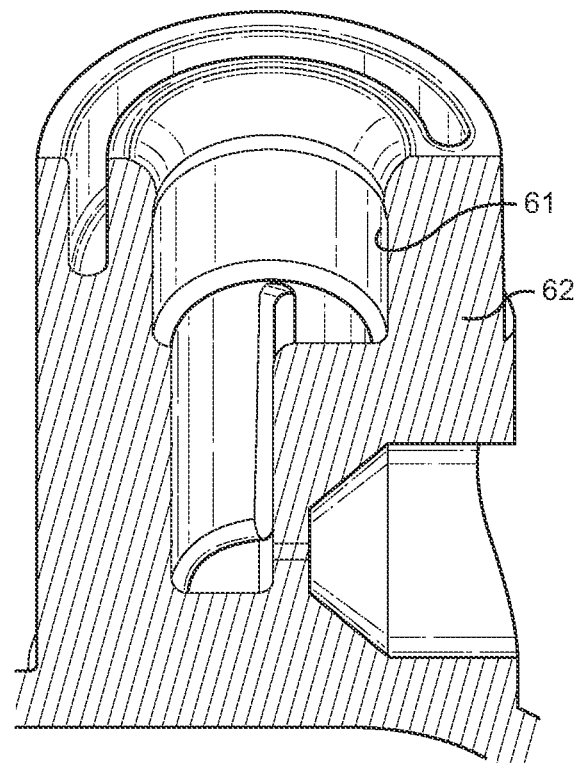

As shown in FIGS. 15A and 15B, the valve stem block 62 has the cylindrical inner bore 61 which has an inner diameter BD1 which has a first diameter, a seal 224 at an entrance to the inner bore 61 having a second diameter BD2 which is smaller than the first diameter. The seal 224 is inwardly convex and/or is toroidal. The first diameter BD1 is about 3.22 mm and is about 3.5% larger than the second diameter BD2. The valve system 54 has a cylindrical outer surface 226 (FIG. 2) with a diameter which is smaller than the first diameter BD1 but larger than the second diameter BD2 prior to introduction of the valve stem 54 into the inner bore 61 and is about 1% larger. The valve stem block 62 also includes an annular recess 228 which extends more than half way around the periphery of the inner bore 61, in this embodiment about 350° or more. The annular recess 228 has an inner diameter which is about 40% larger than the inner diameter BD1 of the cylindrical inner bore 61. This arrangement has been found to provide extremely effective sealing against blowback which has occurred in prior designs which have a substantially greater interference fit between the exterior diameter of the valve stem and the interior diameter of the inner bore of the valve stem. Surprisingly, and advantageously, using the inwardly convex seal 224 to the bore 61, very effective sealing without any blowback can be achieved even with a relatively small interference fit between the valve stem 54 and the seal 224, the annular recess 228 assisting in providing resilience to the valve stem block 62 for this purpose. The small interference fit allows for good sealing even when the inhaler 10 is subjected to high temperatures for long periods since there is little stress to relieve.

Furthermore, the seal 224 permits a relatively low insertion force for inserting the valve stem 54 into the valve stem block 62 and this enables accurate positioning of these two components relative to one another in an axial direction of the valve stem 54 so that the dose counter system 24 can count reliably by way of accurate actuation of its actuator pin 26 by the canister ferrule 220.

Figure 16A:
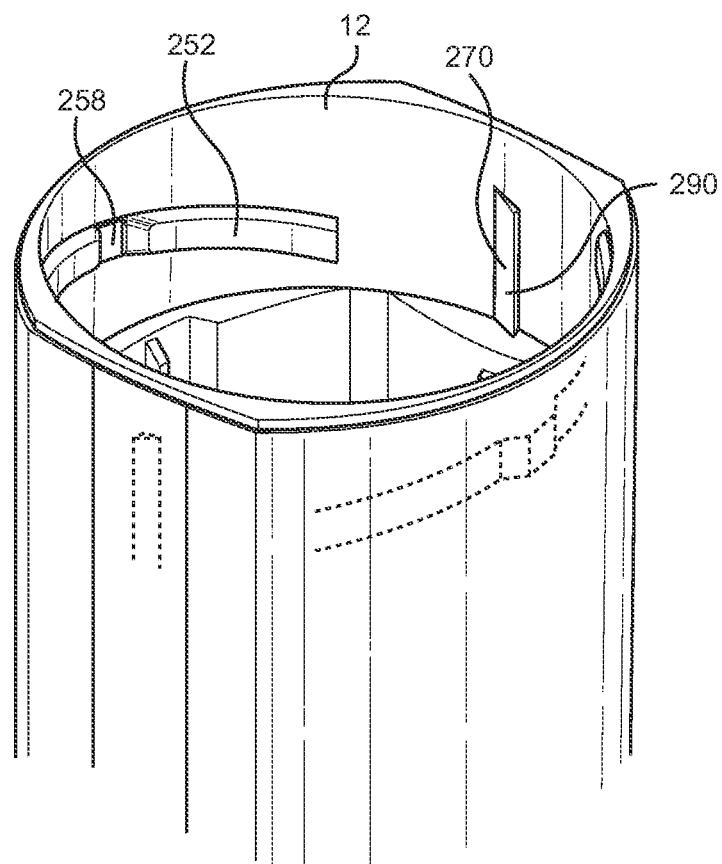
FIGS. 16A, 16B, 17A, 17B, 17C, 17D, 18A, 18B and 18C show various views of part of the inhaler, including components showing the interlocking interaction of the main body of the inhaler with a cap housing thereof.
Figure 16B:
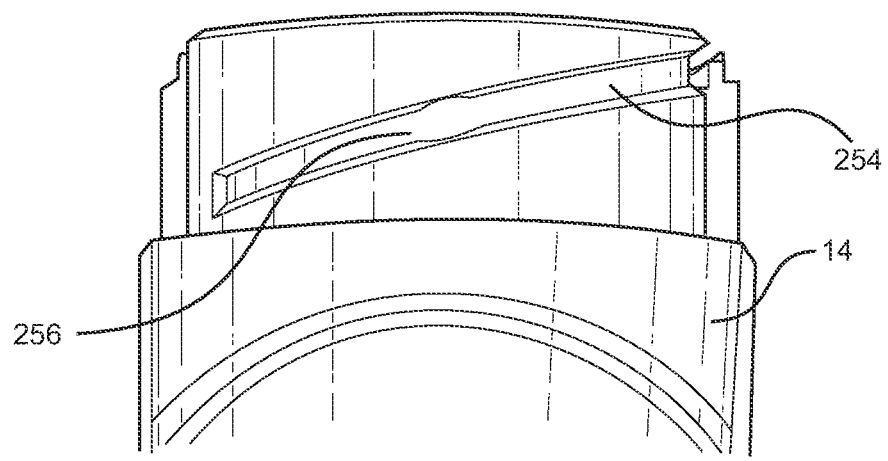

As shown in the various sectional views of FIGS. 16A through to 18C, a lock system 250 is provided for locking the cap housing or force holding unit housing 12 on the main body 14. Helical threads 252, 254 are provided, with male threads 252 on the cap housing 12 and female threads 254 on the main body 14, for rotational attachment of the cap housing 12 on the main body 14 and for resisting relative longitudinal movement therebetween without rotation.

Figure 17A:
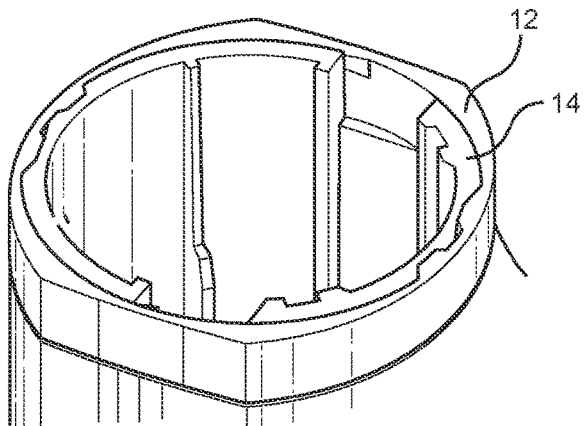
Figure 17B:
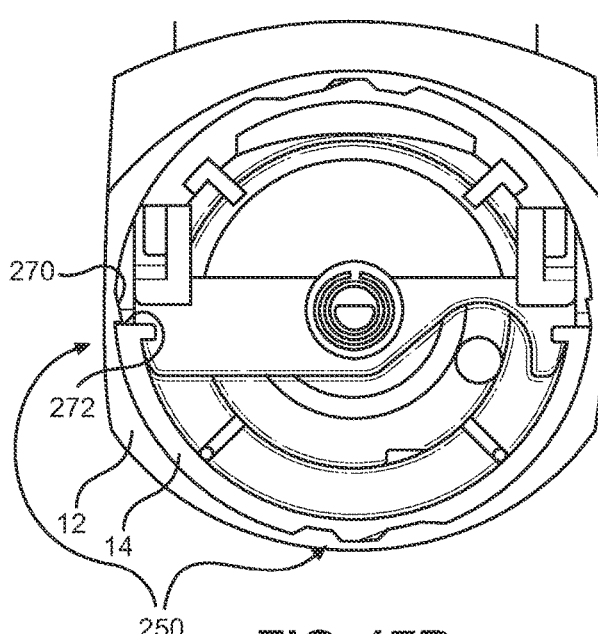
Figure 17C:
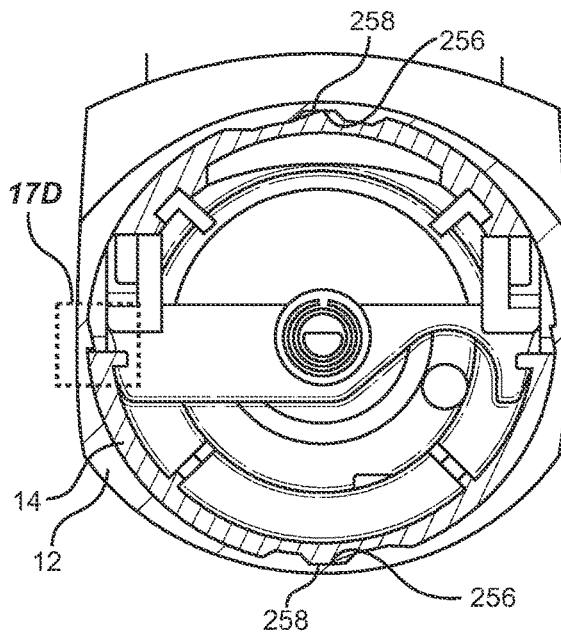
Figure 17D:
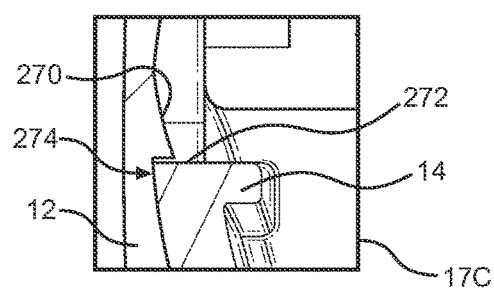
Figure 18A:
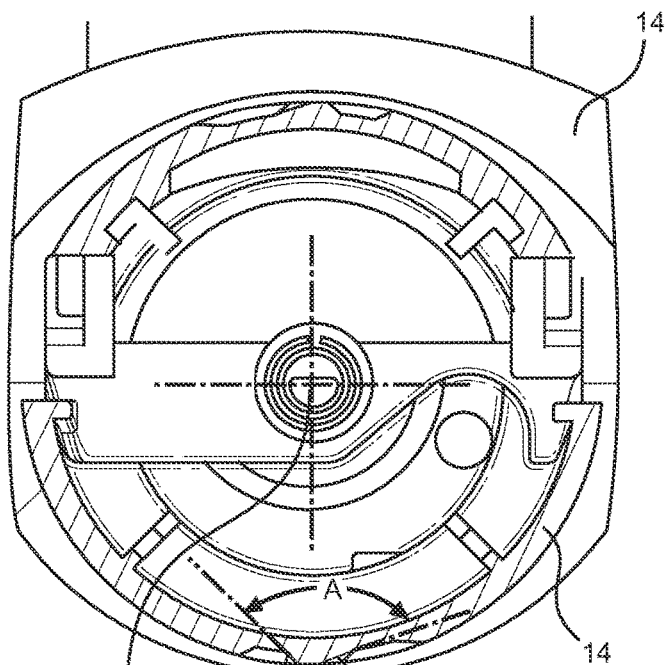
Figure 18B:
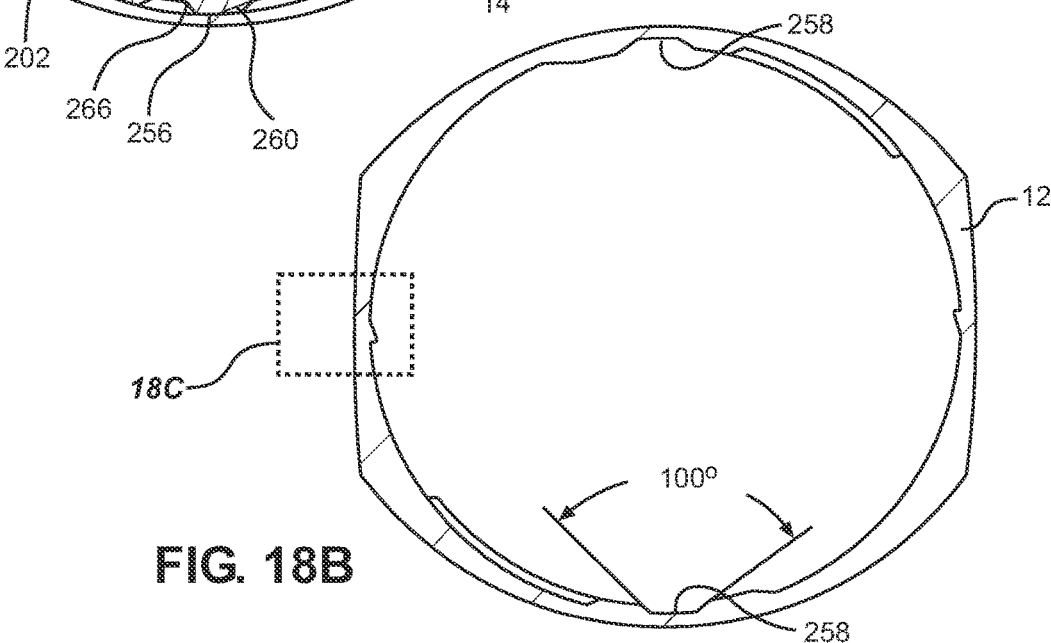
Figure 18C:
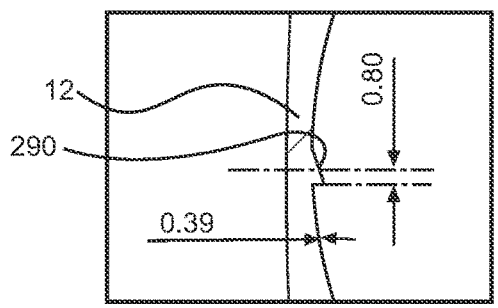

The lock system 250 includes a protrusion 256 in the region of the helical thread 254 on the main body 14 which is lockable in a recess 258 in the region of the helical thread 252 on the cap housing. As shown in FIG. 17C, the inhaler 10 includes two of the protrusions 256 in two of the recesses 258 formed at opposing locations on the inhaler, i.e. diametrically opposite to one another. As shown in FIG. 18A, each protrusion 256 has a leading ramp surface 260 and a trailing ramp surface 266, the included angle A between the ramp and trailing surfaces 260, 266 being 115°, although a range of about 95 to 120° is envisaged. The recesses have a similar included angle which is smaller than the angle of the protrusion 256 at about 100°. This ensures that the protrusion 256 will fit securely in the recess 258 without any play rotationally.

The main body 14 has a central axis 202 coincident with that 202 of the valve stem block 62 and the ramp surfaces 266 are inclined at an angle of about 45°±15° to tangential.

The lock system 250 also includes a first lock member 270 on the cap housing 12 which is adapted to engage a second lock member 272 at a lock interface 274 formed by respective engagement faces thereof, the lock interface 274 being oriented substantially perpendicular to tangential. This therefore assists in preventing rotation. The first lock member 270 has a radial extent of 0.39 mm, although about 0.35 to 0.45 mm is envisaged in other embodiments or 0.25 to 0.75 mm. The second lock member 272, it will be appreciated, has a greater radial extent. The first lock member 270 has a longitudinal extent parallel to the axis 202 of about 10 mm.

The main body 14 and cap housing 12 are formed of plastics material and the lock system 250 is configured so that a release torque required to overcome the locking provided by the plastics main body and cap housing at the lock interface 274 and at the protrusions 256 and recesses 258 is more than 1 Nm. In the described example, the release torque is about 2.75 Nm. When an information sticker is applied over the top of the interface between the main body 14 and cap housing 12 the release torque may rise to about 3.5 Nm. This has been found to be lower than 4 Nm and this is low enough that a laboratory is capable of opening up the inhaler 10 for inspection without significant destruction. However, this level of torque is significantly higher than likely to be tried by a user in an attempt to open the inhaler 10 which might result in tampering and damage to the components of the inhaler 10.

In an alternative design, the radial extent of the first locking member 270 is significantly greater at about 0.73 mm and this has been found, surprisingly, to provide a removal torque which is considered too high at 4.6 Nm for laboratory disassembly without destruction. In contrast, a design omitting the first lock member 270 was found to provide a removal torque of only 0.7 Nm which is considerably too low and likely to result in users rotating the cap housing 12 off the main body 14 and potentially damaging the inhaler by investigating the contents. In fact, this was the first design attempted by the present inventors and the next step was to double up the number of protrusions 256 and recesses 258 so that there are four in total in an attempt to double the torque, at least, from 0.7 Nm. However, surprisingly, with this design, the removal torque was only increased by about 10% to 0.8 Nm. The ideal remove torque was surprisingly achieved with only one protrusion 256 on each thread 254 and with a locking member 270 with only a small radial extent of 0.39 mm. The locking member 270 advantageously also includes a lead ramp 290 for achieving a smooth snap lock of the cap housing 12 onto the main body 14 when the cap housing 12 is twisted into the locked position.

Figure 19:
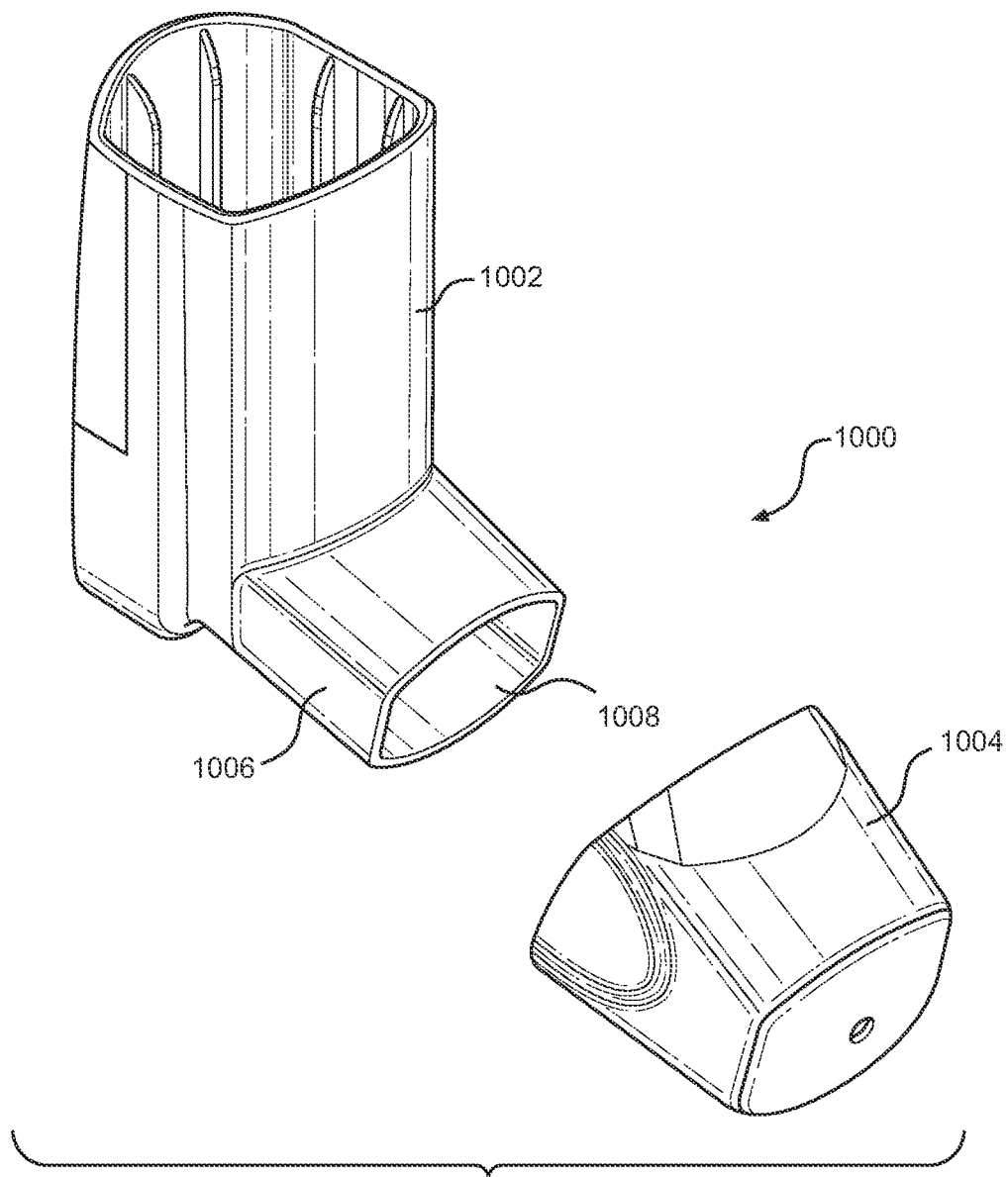
FIG. 19 shows a modified form of the inhaler of FIG. 1A in which the force holding unit and cap housing are removed and the modified inhaler takes up the form of a metered dose inhaler.

FIG. 19 shows a modification of the inhaler 10 to form an inhaler 1000 which is a metered dose inhaler having a main body 1002 and mouthpiece dust cap 1004 for the mouthpiece 1006 for stopping foreign objects entering the central bore 1008 of the mouthpiece 1006 and for protecting the mouthpiece generally. This metered dose inhaler 1000 does not include the cap housing 12 or the force holding unit 30 or yoke 56 but it does include the same dose counter chamber 22, dose counter system 24, canister 50 and metering valve 52 and valve stem 54 and valve stem block 62 as that in the inhaler 10. If this metered dose inhaler is left with the canister 50 accidentally depressed, for example while squashed in luggage or clothing by mistake, such that the metering chamber is left exposed to the atmosphere for a considerable period of time, then when the inhaler 1000 is located and turned upright for use with respective gravity with the canister allowed to extend to its rest position in which the metering chamber communicates with the interior reservoir, any gas such as air which has entered the metering chamber is easily expelled up into the interior reservoir of the canister just as in the inhaler 10 such that an accurate next dose is applied and the problem of gas lock is therefore avoided.

Inhalers in accordance with preferred embodiments of the present invention are suitable for the delivery of many classes of active ingredients by inhalation, and may be used for the treatment of various diseases and disorders. According to preferred embodiments, the inhaler is used for the treatment of respiratory disorders (e.g., COPD, asthma and/or cystic fibrosis). The inhaler may also be used to treat non-respiratory disorders, such as migraine. According to an embodiment, a method of treating a respiratory disease or disorder comprises actuating the inhaler to administer a therapeutically effective amount of one or more active ingredients. As described herein, the canister of the inhaler contains a drug formulation comprising one or more active ingredients in suspension or in solution.

Preferably, the drug formulation comprises one or more active ingredients in propellant (e.g., HFA). The drug formulation may optionally comprise one or more excipients in combination with the active ingredient(s) and propellant.

In certain embodiments, the inhaler described herein can be used to treat patients suffering from a disease or disorder selected from asthma, chronic obstructive pulmonary disease (COPD), exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, and any other respiratory disease, condition, trait, genotype or phenotype that can respond to the administration of, for example, a long-acting muscaric antagonist (LAMA), long-acting $\beta$2-adrenergic agonist (LABA), corticosteroid, or other active agent as described herein, whether alone or in combination with other therapies. In certain embodiments, the compositions, systems and methods described herein can be used to treat pulmonary inflammation and obstruction associated with cystic fibrosis. As used herein, the terms "COPD" and "chronic obstructive pulmonary disease" may encompass chronic obstructive lung disease (COLD), chronic obstructive airway disease (COAD), chronic airflow limitation (CAL) and chronic obstructive respiratory disease (CORD) and include chronic bronchitis, bronchiectasis, and emphysema. As used herein, the term "asthma" refers to asthma of whatever type or genesis, including intrinsic (non-allergic) asthma and extrinsic (allergic) asthma, mild asthma, moderate asthma, severe asthma, bronchitic asthma, exercise-induced asthma, occupational asthma and asthma induced following bacterial infection. Asthma is also to be understood as embracing wheezy-infant syndrome.

A range of classes of active ingredients have been developed to treat respiratory disorders and each class has differing targets and effects.

Bronchodilators are employed to dilate the bronchi and bronchioles, decreasing resistance in the airways, thereby increasing the airflow to the lungs. Bronchodilators may be short-acting or long-acting. Typically, short-acting bronchodilators provide a rapid relief from acute bronchoconstriction, whereas long-acting bronchodilators help control and prevent longer-term symptoms.

Different classes of bronchodilators target different receptors in the airways. Two commonly used classes are anticholinergics and $\beta$2-agonists.

Anticholinergics (or "antimuscarinics") block the neurotransmitter acetylcholine by selectively blocking its receptor in nerve cells. On topical application, anticholinergics act predominantly on the M3 muscarinic receptors located in the airways to produce smooth muscle relaxation, thus producing a bronchodilatory effect. Non-limiting examples of long-acting muscarinic antagonists (LAMA's) include tiotropium (bromide), oxitropium (bromide), aclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate), darifenacin (hydrobromide) and umeclidinium (bromide). In each case, particularly preferred salt/ester forms are indicated in parentheses.

$\beta$2-Adrenergic agonists (or "$\beta$2-agonists") act upon the $\beta$2-adrenoceptors and induce smooth muscle relaxation, resulting in dilation of the bronchial passages. Non-limiting examples of long-acting $\beta$2-adrenergic agonists (LABA's) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). Non-limiting examples of short-acting $\beta$2-agonists (SABA's) include albuterol (sulfate) and levalbuterol (tartrate). In each case, particularly preferred salt/ester forms are indicated in parentheses.

According to one embodiment, the formulation comprises albuterol (sulfate).

Another class of active ingredients employed in the treatment of respiratory disorders are inhaled corticosteroids (ICS's). ICS's are steroid hormones used in the long-term control of respiratory disorders. They function by reducing the airway inflammation. Non-limiting examples of inhaled corticosteroids include budesonide, beclomethasone (dipropionate), fluticasone (propionate), mometasone (furoate), ciclesonide and dexamethasone (sodium).

According to one embodiment, the formulation comprises beclomethasone dipropionate.

According to an embodiment, the inhaler delivers one or more active ingredients selected from the group consisting of tiotropium (bromide), oxitropium (bromide), aclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate), darifenacin (hydrobromide), umeclidinium (bromide), formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride), vilanterol (triphenylacetate), albuterol (sulfate), levalbuterol (tartrate), budesonide, beclomethasone (dipropionate), fluticasone (propionate), mometasone (furoate), ciclesonide, dexamethasone (sodium) and a combination thereof.

According to particular embodiments, the inhaler delivers a combination of at least two different active ingredients (two, three, four, etc.) which belong to the same or different classes. According to one embodiment, the inhaler delivers a "triple combination" of three different active ingredients. The three active ingredients may belong to three different active ingredient classes (e.g., LAMA, LABA, ICS); alternatively, two or three of the active ingredients may belong to the same class.

According to additional embodiments, the inhaler delivers one or more active ingredients selected from the group consisting of a long-acting muscarinic antagonist (LAMA), a long-acting β2-adrenergic agonist (LABA), an inhaled corticosteroid (ICS) and a combination thereof. Thus, the inhaler may deliver a formulation comprising one or more LAMA's, one or more LABA's and one or more ICS's. That is, the device may deliver a double combination of a LAMA and a LABA, a LAMA and an ICS, or a LABA and an ICS; or a triple combination of a LAMA, a LABA and an ICS.

According to an alternative embodiment, the inhaler delivers one or more active ingredients for the treatment of a headache disorder, such as migraine. For example, the inhaler may deliver dihydroergotamine (DHE) or a pharmaceutically acceptable salt thereof, such as dihydroergotamine mesylate.

In one embodiment the inhaler comprises a reservoir, particularly a pressurized canister, comprising an active ingredient.

Preferably the active ingredient is presented in a pharmaceutical formulation comprising a propellant, optionally a co-solvent and optionally other pharmaceutically acceptable excipients.

Preferred propellants include hydrofluroalkanes, in particular 1,1,1,2-tetrafluoroethane (HFA134a), 1,1,1,2,3,3,3-heptafluoropropane (HFA227), or combinations thereof. Most particular propellant is HFA134a. Most particular HFA134a concentration is from about 91.8% w/w to 92.9% w/w.

HFA134a has a low boiling point (−26.1° C.) and correspondingly high vapor pressure (572 kpa) at 20° C.

Particular co-solvents are selected from the list of aliphatic alcohols (particularly ethanol), glycerols and glycols. Most particular co-solvent is ethanol. Most particular ethanol concentration is about 8% w/w.

Ethanol is well known to be compatible with HFA-134a and increases the solubility of BDP. Ethanol (anhydrous) is used as a co-solvent to aid solubility of BDP in HFA134a. A concentration of around 8% w/w of ethanol is known to provide necessary stability, preventing precipitation and achieving correct aerosol performance.

Other pharmaceutically acceptable excipients include surfactants, particularly oleic acid.

Preferably, the active ingredient is suspended in the propellant. Alternatively the active ingredient is dissolved in the propellant. The active ingredient may also be partly suspended and partly dissolved in the propellant.

A particular active ingredient is selected from the group consisting of anti-inflammatory agents, β2-adrenoreceptor agonists, anti-cholinergic agents, anti-histamines, serotonin agonists, and combinations thereof.

A particular corticosteroid is beclomethasone dipropionate (BDP).

A particular β2-adrenoreceptor agonist is salbutamol sulphate.

In a particular embodiment of the invention, the active ingredient is selected from beclomethasone dipropionate (BDP), salbutamol sulphate and dihydroergotamine.

In a particular embodiment the inhaler comprises a pressurized canister comprising beclomethasone dipropionate as active ingredient, HFA134a as propellant and ethanol as co-solvent.

In a particular embodiment the inhaler comprises a pressurized canister comprising beclomethasone dipropionate as active ingredient at about 1.0 mg/ml, HFA134a as propellant at about 1090.20 mg/ml and ethanol as co-solvent at about 94.80 mg/ml.

In a particular embodiment the inhaler comprises a pressurized canister comprising beclomethasone dipropionate as active ingredient at about 0.084% w/w, HFA134a as propellant at about 91.9% w/w and ethanol as co-solvent at about 8.0% w/w.

In a particular embodiment the inhaler comprises a pressurized canister comprising beclomethasone dipropionate as active ingredient at about 0.169% w/w, HFA134a as propellant at about 91.8% w/w and ethanol as co-solvent at about 8.0% w/w.

In a particular embodiment the inhaler comprises a pressurized canister comprising salbutamol sulphate as active ingredient, HFA134a as propellant and ethanol as co-solvent.

In a particular embodiment the inhaler comprises a pressurized canister comprising about 0.1098 mg of salbutamol sulphate as active ingredient, about 27.8 mg of HFA134a as propellant and about 3.6 mg of ethanol as co-solvent.

One embodiment relates to an inhaler as described herein comprising an active ingredient.

One embodiment relates to an inhaler as described herein comprising an active ingredient for therapeutic use.

One embodiment relates to an inhaler as described herein comprising an active ingredient for use in the treatment or prevention of a respiratory disease, particularly COPD or Asthma.

One embodiment relates to an active ingredient for use in the treatment or prevention of a respiratory disease, particularly COPD or Asthma, wherein the active ingredient is delivered to a patient using an inhaler as described herein.

One embodiment relates to a method for the treatment or prevention of respiratory diseases, particularly COPD or Asthma, which method comprises administering an active ingredient to a human being or animal using an inhaler as described herein.

One embodiment relates to the use of an inhaler as described herein comprising an active ingredient for the treatment or prevention of respiratory diseases, particularly COPD or Asthma.

Embodiments of the present invention may be further understood by reference to the Example provided below.

EXAMPLE

According to the following example, a method of using the inhaler of the present invention comprises delivering a therapeutically effective amount of beclomethasone dipropionate HFA for the treatment of asthma, particularly for the maintenance treatment of asthma as prophylactic therapy in patients 4 years of age and older, wherein the inhaler is a breath-actuated inhaler (BAI) as described herein and the step of actuating the inhaler comprises inhaling through the inhaler. The breath-actuated inhaler may be used by patients to deliver at least about 40 mcg beclomethasone dipropionate upon each actuation, preferably twice daily, e.g., it may be used by patients 4 to 11 years old to deliver 40 mcg or 80 mcg beclomethasone dipropionate twice daily, or may be used by patients 12 years of age and older to deliver 40 mcg, 80 mcg, 160 mcg or 320 mcg beclomethasone dipropionate twice daily. Actuation of the breath-actuated inhaler is preferably triggered by an inspiratory flow rate of at least about 20 liters per minute (L/min), and includes a primeless valve so that no priming actuations are required before use. A method of treating asthma may comprise inhaling through the BAI at a flow rate of at least about 20 L/min without priming the inhaler before use, wherein the inhaler comprises a primeless valve as described herein and wherein the mean change from baseline for $FEV_1$ between 2-6 weeks or between 2-12 weeks or between 4-12 weeks of using the BAI is greater than about 0.150 L or greater than about 0.200 L. Preferably, the mean peak plasma concentration (Cmax) of BDP is between about 6000 pg/mL and about 7000 pg/mL or between about 6200 pg/mL and about 6800 pg/mL at 2 minutes after inhalation of 320 mcg using the BAI (4 inhalations of the 80 mcg/inhalation strength). The mean peak plasma concentration of the metabolite 17-BMP is preferably between about 1000 pg/mL and about 2000 pg/mL or between about 1200 pg/mL and about 1700 pg/mL at 10 minutes after inhalation of 320 mcg of the BAI.

The breath-actuated inhaler (BAI) in this example included a canister having an interior reservoir containing pressurised inhalable substances including fluid; a "primeless" metering valve including a metering chamber and a valve stem defining a communication path between the metering chamber and the interior reservoir, the communication path including an opening configured to permit flow between a transfer space inside the valve stem and the interior reservoir, the interior reservoir being arranged for orientation above the metering chamber whereby gas such as air located within the metering chamber is replaced with liquid from the interior reservoir. Preferably, the primeless metering valve is the embodiment shown in FIG. 4 and described in U.S. Pat. No. 7,959,042B. Alternatively, the primeless metering valve is similar to the embodiment shown in FIG. 4 of US2016/0084385, as described herein.

Two confirmatory Phase 3 clinical trials were conducted comparing the above-described breath-actuated inhaler with placebo in adult and adolescent patients with persistent asthma (Trial 1 and Trial 2).

Trial 1: This randomized, double-blind, parallel-group, placebo-controlled, 12-week, efficacy and safety trial compared the breath-actuated inhaler 40 and 80 mcg given as 1 inhalation twice daily with placebo in adult and adolescent patients with persistent symptomatic asthma despite low-dose inhaled corticosteroid or non-corticosteroid asthma therapy. Patients aged 12 years and older who met the entry criteria including $FEV_1$ 40-85 percent of predicted normal, reversible bronchoconstriction of 15% with short-acting inhaled beta-agonist entered a 14-21 day run-in period. 270 patients (104 previously treated with inhaled corticosteroids) who met all the randomization criteria including asthma symptoms and rescue medication use were discontinued from asthma maintenance medication and randomized equally to treatment with the breath-actuated inhaler (BAI) 80 mcg/day BDP, the breath-actuated inhaler 160 mcg/day BDP or placebo. Baseline $FEV_1$ values were similar across treatments. The primary endpoint for this trial was the standardized baseline-adjusted trough morning forced expiratory volume in 1 second ($FEV_1$) area under the effect curve from time zero to 12 weeks [$FEV_1$ AUEC(0-12 wk)]. Patients in both treatment groups had significantly greater improvements in trough $FEV_1$ compared to placebo (BAI 80 mcg/day, LS mean change of 0.124 L and BAI 160 mcg/day, LS mean change of 0.116 L over 12 weeks). In addition, the mean change from baseline for $FEV_1$ was greater than about 0.150 L between week 4 through week 12 (generally between about 0.150 L and about 0.250 L). Both doses of BAI were effective in improving asthma control with significantly greater improvements in $FEV_1$ and morning PEF when compared to placebo. Reduction in asthma symptoms was also supportive of the efficacy of the BAI.

Trial 2: This randomized, double-blind, parallel-group, placebo-controlled, 6-week, efficacy and safety trial compared BAI 40 and 80 mcg BDP given as 4 inhalations twice daily and placebo in adult and adolescent patients with persistent symptomatic asthma despite treatment with non-corticosteroid, inhaled corticosteroids (with or without a long acting beta agonist [LABA]), or combination asthma therapy. The study also included a reference treatment group, QVAR® Inhalation Aerosol (QVAR MDI) 40 mcg, 4 inhalations twice daily. Patients aged 12 years and older who met the entry criteria including $FEV_1$ 50-90% predicted normal, reversible bronchoconstriction of at least 10% with short-acting inhaled beta-agonist discontinued baseline asthma treatment and entered a 2-4 week run-in period. 425 patients (257 previously treated with ICS with or without LABA) who met all the randomization criteria including $FEV_1$ of 40-85% predicted and 15% reversibility with short-acting inhaled beta-agonist, and asthma symptoms were randomized equally to the BAI 320 mcg/day, BAI 640 mcg/day, QVAR MDI 320 mcg/day or placebo. Baseline $FEV_1$ values were similar across treatments. The primary endpoint for this trial was the standardized baseline-adjusted trough morning forced expiratory volume in 1 second ($FEV_1$) area under the effect curve from time zero to 6 weeks [$FEV_1$ AUEC(0-6wk)]. Patients in both treatment groups had significantly greater improvements in trough $FEV_1$ compared to placebo (BAI 320 mcg/day, LS mean change of 0.144 L and BAI 640 mcg/day, LS mean change of 0.150 L over 12 weeks). Treatment with QVAR MDI was similar. The change from baseline in morning $FEV_1$ during the trial was greater than 0.150 L or 0.200 L between week 2 through week 6 (generally between about 0.150 L and about 0.250 L). Both doses of the BAI were effective in improving asthma control with significantly greater improvements in $FEV_1$, morning PEF, weekly average of daily trough morning $FEV_1$, reduced rescue medication use and improved asthma symptom scores than with placebo. Similar results were demonstrated with QVAR MDI.

The inhaler of the present disclosure has broad application. The apparatuses and associated methods in accordance with the present disclosure have been described with reference to particular embodiments thereof in order to illustrate the principles of operation. The above description is thus by way of illustration and not by way of relative and directional references (including: upper, lower, upward, downward, left, right, leftward, rightward, top, bottom, side, above, below, front, middle, back, vertical, horizontal, height, depth, width, and so forth) are normally given by way of example to aid the reader's understanding of the particular embodiments described herein. They should not be read to be requirements or limitations, particularly as to the position, orientation, or use of the invention unless specifically set forth in the claims. Connection references (e.g., attached, coupled, connected, joined, secured and the like) are to be construed broadly and may include intermediate members between a connection of elements and relative movement between elements. As such, connection references do not necessarily infer that two elements are directly connected and in fixed relation to each other, unless specifically set forth in the claims.

Various modifications may be made to the embodiments described without departing from the scope of the invention as defined by the accompanying claims.

What is claimed is:

1. An inhaler for the inhalation of inhalable substances, the inhaler comprising:
    a main body and a cap housing defining an interior chamber;
    a canister enclosed within the interior chamber having an interior reservoir containing pressurised inhalable substances including fluid;
    a metering valve including a metering chamber and a valve stem defining a communication path between the metering chamber and the interior reservoir, the communication path including an first opening configured to permit flow between a transfer space inside the valve stem and the interior reservoir, the interior reservoir being arranged for orientation above the metering chamber whereby gas located within the metering chamber is replaced with liquid from the interior reservoir; and
    wherein a lock system is provided for locking the cap housing on the main body;
    the lock system including helical threads having non-overlapping and distinct thread segments for providing rotational attachment of the cap housing to the main body and a first lock member that cooperates with a second lock member to achieve a snap lock between the cap housing and the main body when the cap housing is rotationally attached to the main body in a locked position;
    wherein the thread segments are radially disposed about a central axis and arranged such that the thread segments are non-overlapping with respect to each other along the central axis; and
    wherein the first lock member is interposed between the thread segments.

2. The inhaler of claim 1, wherein the lock system is configured to resist relative longitudinal movement between the cap housing and the main body; and to resist rotation of the cap housing relative to the main body.

3. The inhaler of claim 1, wherein helical threads are provided for rotational attachment of the cap housing on the main body; and wherein the lock system includes a protrusion in a region of a helical thread on one of the main body and the cap housing which is lockable in a recess in a region of a helical thread on the other of the main body and the cap housing.

4. The inhaler of claim 1, in which the main body and the cap housing are formed of plastics material and the lock system is configured so that a release torque required to overcome the locking provided by the plastics main body and cap housing is more than 1 Nm.

5. The inhaler of claim 4, wherein the release torque required to overcome the locking provided by the plastics main body and cap housing is lower than 4 Nm.

6. The inhaler of claim 1, in which the lock system is configured such that a release torque is between 2 and 5 Nm.

7. The inhaler of claim 1, in which the communication path is configured to permit liquid to flow under pressure along the communication path to the metering chamber and gas to flow in a reverse direction therealong from the metering chamber into the interior reservoir.

8. The inhaler of claim 1, in which the first opening comprises an elongated opening.

9. The inhaler of claim 8, which includes a second opening or further openings into the communication path.

10. The inhaler of claim 9, in which the second opening is diametrically opposed to the first opening.

11. The inhaler of claim 1, in which the valve stem has at least one opening into the interior reservoir with an axially oriented portion facing directly axially along a longitudinal axis of the valve stem into the interior reservoir for the flow of fluid directly into the communication path in an axial direction along the valve stem.

12. The inhaler of claim 1, which includes a metering chamber exit port for venting the metering chamber to atmosphere via a stem block and/or nozzle.

13. The inhaler of claim 1, including a canister fire system enclosed in the interior chamber defined by the main body and the cap housing for ejecting inhalable substances from the inhaler in response to air flow by closing communication between the metering chamber and the interior reservoir and opening communication between the metering chamber and atmosphere.

14. The inhaler of claim 13, wherein the inhaler includes a drive for driving the canister relative to the valve stem.

15. The inhaler of claim 14, the drive including a drive spring.

16. The inhaler of claim 13, wherein the canister fire system is adapted to depress the valve stem into the canister to cause inhalable substances to be ejected from the inhaler and to hold the valve stem depressed with the metering chamber communicating with atmosphere.

17. The inhaler of claim 16, in which the canister fire system includes a reset actuator which is operable so as to extend the valve stem relative to the canister in order to close communication between atmosphere and the metering chamber and to open communication between the metering chamber and the interior reservoir.

18. The inhaler of claim 17, in which the reset actuator comprises a mouthpiece cap for a mouthpiece of the inhaler, the mouthpiece cap being closable to permit extension of the valve stem relative to the canister.

19. The inhaler of claim 18, which includes a preventer adapted, after an inhalation has taken place, to prevent a further inhalation until the mouthpiece cap has been closed to extend the valve stem.

20. The inhaler of claim 19, in which the preventer comprises a warning signaller comprising at least one of, an audible alarm, a visual alarm, a dose counter or a warning notice.

21. The inhaler of claim 1, wherein the inhaler includes an actuator system for operating a drive.

22. The inhaler of claim 21, in which the actuator system is actuable by air flow.

23. The inhaler of claim 1, wherein the inhalable substances comprise at least one propellant.

24. The inhaler of claim 1, which includes a dose counter for counting doses.

25. The inhaler of claim 24, wherein the dose counter is configured to count one count for each inhalation of a dose.

26. The inhaler of claim 24, in which the dose counter includes: (a) a tape bearing dose indicia for displaying counts and/or (b) an actuator pin for contact with the canister, or a body movable therewith, for counting doses, the actuator pin extending out of a dose counter chamber through an aperture in a wall for contact during counting with the canister.

27. The inhaler of claim 26, further comprising a barrier configured to separate a dose counter chamber from an inner space of the inhaler for containing the canister.

28. The inhaler of claim 27, wherein the inhaler is a nasal inhaler, and the barrier comprises a stepped barrier having a vertical surface and a horizontal surface and the dose counter is coupled to at least one of the vertical surface and the horizontal surface.

29. The inhaler of claim 1, wherein the inhaler is a breath actuated inhaler.

30. The inhaler of claim 1, wherein the inhaler is a metered dose inhaler.

31. The inhaler of claim 1, wherein the inhaler is an oral inhaler.

32. The inhaler of claim 1, wherein the inhaler is a nasal inhaler.

33. The inhaler of claim 1, which includes a reset actuator which when actuated prevents exposure of the metering chamber to atmosphere, wherein the inhaler provides 75 to 125% of labelled claim for a dose following exposure of the metering chamber to atmosphere for a time period which is more than one minute.

34. The inhaler of claim 33, in which the inhaler provides 75 to 125% of labelled claim for a dose following exposure of the metering chamber to atmosphere for a time period which is more than two minutes.

35. The inhaler of claim 33, in which the inhaler provides 75 to 125% of labelled claim for a dose following exposure of the metering chamber to atmosphere for a time period which is one hour, more than one hour, 24 hours or more than 24 hours.

36. The inhaler of claim 33, in which the reset actuator is a mouthpiece cap that, when closed, prevents exposure of the metering chamber to atmosphere.

37. The inhaler of claim 1, which includes a metering valve spring and an opposing canister spring for drivingly firing the canister, the metering valve spring, canister spring and metering valve being arranged in the inhaler such that an equilibrium of various forces is achieved in at least one ready-to-fire configuration of the inhaler.

38. The inhaler of claim 37, which is adapted to operate including at least one suction force.

39. The inhaler of claim 38, wherein the suction force operates against the canister spring.

40. The inhaler of claim 1, wherein the inhaler is a nasal inhaler and the nasal inhaler comprises a nosepiece cap coupled to the main body, the nosepiece cap moveable with respect to the main body from a closed position to an open position; and a yoke coupled to the main body and the canister, the yoke moveable from a first position to a second position as the nosepiece cap moves from the closed position to the open position, wherein the canister moves with respect to the main body as the yoke moves from the first position to the second position.

41. The inhaler of claim 40, wherein the nosepiece cap includes a cam and the yoke includes a leg engageable with the cam such that rotation of the nosepiece cap causes movement of the yoke.

42. The inhaler of claim 40, wherein the canister is moveable in a dispensing direction from a storage position to a dispensing position, and wherein the canister moves in the dispensing direction as the yoke moves with respect to the housing.

43. The inhaler of claim 1, in which the lock system is configured such that a release torque is lower than 4 Nm.

44. The inhaler of claim 1, in which the lock system is configured such that a release torque is between 2.5 and 3 Nm.

* * * * *